United States Patent
Goldberg et al.

(10) Patent No.: US 7,384,914 B2
(45) Date of Patent: Jun. 10, 2008

(54) NIGHT-TIME ORAL INSULIN THERAPY

(75) Inventors: Michael Goldberg, Tarrytown, NY (US); Ehud Arbit, Tarrytown, NY (US)

(73) Assignee: Emisphere Technologies, Inc., Cedar Knolls, NJ (US)

( * ) Notice: Subject to any disclaimer, the term of this patent is extended or adjusted under 35 U.S.C. 154(b) by 0 days.

(21) Appl. No.: 10/541,433

(22) PCT Filed: Jan. 6, 2004

(86) PCT No.: PCT/US2004/000273

§ 371 (c)(1), (2), (4) Date: Feb. 16, 2006

(87) PCT Pub. No.: WO2004/062587

PCT Pub. Date: Jul. 29, 2004

(65) Prior Publication Data

US 2006/0178296 A1 Aug. 10, 2006

Related U.S. Application Data

(60) Provisional application No. 60/478,967, filed on Jun. 16, 2003, provisional application No. 60/438,451, filed on Jan. 6, 2003, provisional application No. 60/438,195, filed on Jan. 6, 2003.

(51) Int. Cl.
*A61K 38/28* (2006.01)
(52) U.S. Cl. .......................... 514/3; 530/303; 424/434; 424/439; 424/464; 424/489
(58) Field of Classification Search ................ 530/303; 514/3; 424/434, 439, 464, 489
See application file for complete search history.

(56) References Cited

U.S. PATENT DOCUMENTS

| | | | |
|---|---|---|---|
| 5,698,515 A | 12/1997 | Plate et al. | |
| 6,610,649 B2 | 8/2003 | Wahren et al. | |
| 7,060,675 B2 * | 6/2006 | Ekwuribe et al. | 514/3 |
| 7,084,114 B2 * | 8/2006 | Ekwuribe et al. | 514/3 |
| 7,115,663 B2 * | 10/2006 | Moye-Sherman et al. | 514/559 |
| 7,118,762 B2 * | 10/2006 | Byrd | 424/468 |
| 7,137,951 B2 * | 11/2006 | Pilarski | 600/300 |
| 7,208,178 B2 | 4/2007 | Bhandarkar et al. | |
| 7,227,033 B2 | 6/2007 | Bhandarkar et al. | |
| 2002/0147135 A1 | 10/2002 | Schnell | |

FOREIGN PATENT DOCUMENTS

| | | |
|---|---|---|
| WO | WO 89/06540 | 7/1989 |
| WO | WO 02/02509 | 1/2002 |
| WO | WO 2005/112633 | 12/2005 |

OTHER PUBLICATIONS

Clement Stephen, Diabetes Technology & Therapeutics 4(4), 459-66, 2002.*
Hosny Ehab A., International Journal of Pharmaceutics 237(1-2), 71-6, 2002.*
Mesiha Mounir S., International Journal of Pharmaceutics 249(1-2), 1-5, 2002.*
Miller J. L., Clinical Pharmacology and Therapeutics 53(3), 380-4, 1993.*
Yki-Jarvinen H., Annals of internal medicine 130(5), 389-96, 1999.*
Taton et al., "How recombinant insulin analogs improve insuline therapy of diabetes mellitus: pathophysiology, clinical practice and recommendations", Medical Science Monitor, vol. 7, No. 4, pp. 848-859 (2001).
Gavin et al., "New Classification and Diagnostic Criteria for Diabetes Mellitus", Clinical Cornerstone, vol. 1, No. 3, pp. 1-12 (1998).

* cited by examiner

*Primary Examiner*—David Lukton
(74) *Attorney, Agent, or Firm*—Pearl, Cohen, Zedek, Latzer, LLP

(57) ABSTRACT

A method for protection of a mammal that has impaired glucose tolerance or early stage diabetes mellitus from developing overt or insulin dependent diabetes comprises administering an orally effective dose of a pharmaceutical formulation comprising insulin at nighttime, e.g., at or shortly before bedtime.

59 Claims, 3 Drawing Sheets

|　| C-peptide | | Insulin | | Glucose | |
|---|---|---|---|---|---|---|
| Subject # | Control | pm insulin | Control | pm insulin | control | pm insulin |
| 1 | 3.6 | 1.3 | 20.0 | 7.0 | 117 | 93 |
| 2 | 3.1 | 2.3 | 24.0 | 12.0 | 136 | 176 |
| 3 | 3.4 | 2.6 | 11.8 | 10.0 | 104 | 87 |
| 4 | 2.7 | 2.0 | 8.8 | 7.0 | 117 | 96 |
| 5 | 2.5 | | 6.5 | 5.0 | 221 | 207 |
| 6 | 2.1 | 1.6 | 7.0 | 5.0 | 210 | 226 |
| 7 | 1.8 | 1.6 | 11.0 | 7.0 | 78 | 100 |
| 8 | 1.9 | 2.0 | 8.8 | 8.0 | 199 | 137 |
| 9 | 3.8 | 2.8 | 16.5 | 16.0 | 112 | 126 |
| 10 | 0.9 | 1.2 | 5.0 | 6.0 | 86 | |
| 11 | 2.7 | 2.2 | 17.0 | 12.0 | 173 | |
| 12 | 3.0 | 1.4 | 13.0 | 7.0 | 125 | 107 |
| 13 | 2.9 | 2.3 | 18.0 | 10.0 | 124 | 103 |
| 14 | 1.4 | 1.3 | 9.3 | 5.0 | 123 | 104 |
| 15 | 2.6 | 1.3 | 17.0 | 5.0 | 93 | 78 |
| 16 | 4.9 | 3.3 | 29.0 | 23.0 | 156 | 173 |
| 17 | 2.6 | 2.0 | 19.8 | 12.0 | 144 | 125 |
| 18 | 2.3 | 1.3 | 16.0 | 8.0 | 142 | 121 |
| 19 | 2.6 | 1.9 | 14.0 | 8.0 | 84 | 84 |
| 20 | 2.9 | 3.8 | 5.5 | 14.0 | 123 | 118 |
| Average | 2.69 | 2.01 | 13.90 | 9.35 | 133.35 | 125.61 |
| Std Dev | 0.88 | 0.72 | 6.44 | 4.52 | 40.87 | 42.78 |
| Std Error Mean | 0.20 | 0.16 | 1.44 | 1.01 | 9.63 | 10.08 |
| Ttest | 0.00071 | | 0.00073 | | 0.15361 | |
| | 0.00036 | | 0.00036 | | 0.07681 | |

Figure 1

| Patient No. | Insulin μU/ml night | C-Peptide ng/ml night |
|---|---|---|
| 1 | 20 | 4.9 |
| 2 | 48 | 5.1 |
| 3 | 66 | 7.9 |
| 4 | 12 | 3.1 |
| 5 | 19 | 4.9 |
| 6 | 7 | 2.8 |
| 7 | 41 | 4.7 |
| 8 | 20 | 4.2 |
| 10 | 37 | 6.9 |
| 11 | 9 | 3 |
| 12 | 10 | 4.2 |
| 14 | 17 | 3.7 |
| 15 | 18 | 3.2 |
| 16 | 6 | 1.3 |
| 18 | 7 | 2.8 |
| 19 |  | 4.2 |
| 20 | 22 | 3.6 |
| 22 | 11 | 2.5 |
| 23 | 36 | 4.9 |
| 24 | 37 | 7.5 |

NIGHT-TIME ORAL INSULIN THERAPY

This application is a 371 of PCT/US04/00273, filed Jan. 6, 2004 which claims priority to provisional application 60/438,195, filed Jan. 6, 2003, application 60/438,451, filed Jan. 6, 2003, and application 60/478,967, filed Jun. 16, 2003.

FIELD OF THE INVENTION

This invention relates to the oral delivery of insulin in a therapeutically effective amount to the bloodstream as part of a therapeutic regimen for the treatment of diabetes. This invention further relates to compositions of a delivery agent and insulin for oral administration that facilitates insulin transport in a therapeutically effective amount to the bloodstream for the treatment of diabetes. This invention further relates to the oral administration of dosage forms of insulin and a delivery agent at or shortly before bedtime for the treatment of diabetes.

BACKGROUND OF THE INVENTION

Proteins, peptides and other biological molecules ("biological macromolecules", namely biological polymers such as proteins and polypeptides) are increasingly being use in many diverse areas of science and technology. For example, proteins are employed as active agents in the fields of pharmaceuticals, vaccines and veterinary products. Unfortunately, the use of biological macromolecules as active agents in pharmaceutical compositions is often severely limited by the presence of natural barriers of passage to the location where the active agent is required. Such barriers include the skin, lipid bi-layers, mucosal membranes, severe pH conditions and digestive enzymes.

There are many obstacles to successful oral delivery of biological macromolecules. For example, biological macromolecules are large and are amphipathic in nature. More importantly, the active conformation of many biological macromolecules may be sensitive to a variety of environmental factors, such as temperature, oxidizing agents, pH, freezing, shaking and shear stress. In planning oral delivery systems comprising biological macromolecules as an active agent for drug development, these complex structural and stability factors must be considered. In addition, in general, for medical and therapeutic applications, where a biological macromolecule is being administered to a patient and is expected to perform its natural biological function, delivery vehicles can be used to facilitate absorption through the gastrointestinal tract. These delivery vehicles must be able to release active molecules, at a rate that is consistent with the needs of the particular patient or the disease process.

One specific biological macromolecule, the hormone insulin, contributes to the normal regulation of blood glucose levels through its release by the pancreas, more specifically by the β-cells of a major type of pancreatic tissue (the islets of Langerhans), so that the glucose can be used as a source of energy. Insulin secretion is a regulated process that, in normal subjects, provides stable concentrations of glucose in blood during both fasting and feeding. In normal healthy humans, insulin is secreted from the pancreas into the portal vein, which carries the insulin to the liver. The liver utilizes and/or metabolizes a large portion of the insulin that it receives from the portal circulation.

Blood glucose concentration is the principal stimulus to insulin secretion in healthy humans. Glucose enters the pancreatic β-cell by facilitated transport and is then phosphorylated by glucokinase. Expression of glucokinase is primarily limited to cells and tissues involved in the regulation of glucose metabolism, such as the liver and the pancreatic β-cells. The capacity of sugars to undergo phosphorylation and subsequent glycolysis correlates closely with their ability to stimulate insulin release. It is noted that not all tissues are dependent on insulin for glucose uptake. For example, the brain, kidneys and red blood cells are insulin independent tissues, while the liver, adipose and muscle are insulin dependent tissues.

Diabetes Mellitus ("diabetes") is a disease state in which the pancreas does not release insulin at levels capable of controlling glucose levels and/or in which muscle, fat and liver cells respond poorly to normal insulin levels because of insulin resistance. Diabetes Mellitus is classified into two types: Type 1 and Type 2. Approximately 5 to 10% of diagnosed cases of diabetes are attributed to Type 1 diabetes, and approximately 90% to 95% to type 2 diabetes.

Type 1 diabetes is diabetes that is insulin dependent and usually first appears in young people. In Type 1 diabetes, the islet cells of the pancreas stop producing insulin mainly due to autoimmune destruction and the patient must inject himself with the missing hormone.

Type 2 diabetes is non-insulin dependent diabetes, which may be caused by a combination of insulin resistance (or decreased insulin sensitivity) and, in later stages, insufficient insulin secretion. This is the most common type of diabetes in the Western world. Close to 8% of the adult population of various countries around the world, including the United States, have Type 2 diabetes, and about 30% of these patients will need to use exogenous insulin at some point during their life spans due to secondary pancreas exhaustion and the eventual cessation of insulin production.

Insulin resistance (or decreased insulin sensitivity) is also prevalent in the population, especially in overweight individuals, in those with risk of diabetes (i.e., pre-diabetic, wherein blood glucose levels are higher than normal but not yet high enough to be diagnosed as diabetes) and in individuals with type 2 diabetes who produce enough insulin but whose tissues have a diminished ability to adequately respond to the action of insulin. In order to compensate and overcome the insulin resistance, the pancreatic β-cells initially increase their insulin production such that insulin resistant individuals have high plasma insulin levels. However, after a period of high demand placed on these cells, the cells start to decompensate and exhaust, and insulin secretion is reduced at later stages of diabetes. By the time an individual is diagnosed with type 2 diabetes, roughly 50% of the β-cells have died due to increased demand for insulin production.

Diabetes is the sixth leading cause of death in the United States and accounted for more than 193,000 deaths in 1997. However, this is an underestimate because complications resulting from diabetes are a major cause of morbidity in the population. Diabetes is associated with considerable morbidity and mortality in the form of cardiovascular disease, stroke, digestive diseases, infection, metabolic complications, ophthalmic disorders, neuropathy, kidney disease and failure, peripheral vascular disease, ulcerations and amputations, oral complications, and depression. Thus, diabetes contributes to substantially many deaths that are ultimately ascribed to other causes.

The main cause of mortality with Diabetes Mellitus is long term micro- and macro-vascular disease. Cardiovascular disease is responsible for up to 80% of the deaths of type 2 diabetic patients, and diabetics have a two- to four-fold increase in the risk of coronary artery disease, equal that of patients who have survived a stroke or myocardial infarction. In other words, heart disease, high blood pressure, heart attacks and strokes occur two to four times more frequently in adult diabetics than in adult non-diabetics. This increased risk of coronary artery disease combined with an increase in hypertensive cardiomyopathy manifests itself in an increase in the risk of congestive heart failure. These vascular complications lead to neuropathies, retinopathies and peripheral vascular disease.

Diabetic retinopathy (the breakdown of the lining at the back of the eye) is the leading cause of blindness in adults aged 20 through 74 years, and diabetic kidney disease, e.g., nephropathy (the inability of the kidney to properly filter body toxins), accounts for 40% of all new cases of end-stage renal disease (kidney failure). Furthermore, diabetes is also the leading cause for amputation of limbs in the United States. Diabetes causes special problems during pregnancy, and the rate of congenital malformations can be five times higher in the children of women with diabetes.

Insulin resistance plays an important role in the pathogenesis of hyperglycemia in type 2 diabetes, which eventually induces the development of diabetic complications. Furthermore, insulin resistance ostensibly plays a role in the pathogenesis of macrovascular disease, cardiovascular diseases and microvascular disease.

Poor glycemic control contributes to the high incidence of these complications, and the beneficial effects of tight glycemic control on the chronic complications of diabetes are widely accepted in clinical practice. However, only recently has it been firmly established that elevated blood glucose levels are a direct cause of long-term complications of diabetes. The Diabetes Control and Complications Trial and the United Kingdom Prospective Diabetes Study both showed that control of blood glucose at levels as close to normal as possible prevents and retards development of diabetic retinopathy, nephropathy, neuropathy and microvascular disease.

In type 1 diabetes, insulin therapy is essential and is intended to replace the absent endogenous insulin with an exogenous insulin supply. In type 2 diabetes, therapy has consisted of oral antidiabetic agents, which increase insulin sensitivity and/or insulin secretion, and insulin if, and when, the oral agents fail.

The problem of providing bioavailable unmodified human insulin, in a useful form, to the ever-increasing population of diabetics has occupied physicians and scientists for almost 100 years. Many attempts have been made to solve some of the problems of stability and biological delivery of this peptide. Because insulin is a peptide drug (MW approx. 6000 Da) that is not absorbed in the gastrointestinal tract, it ordinarily requires parenteral administration such as by subcutaneous injection. Thus, most diabetic patients self-administer insulin by subcutaneous injections, often multiple times per day. However, the limitations of multiple daily injections, such as inconvenience, poor patient acceptability, compliance and the difficulty of matching postprandial insulin availability to postprandial requirements, are some of the better-known shortcomings of insulin therapy.

Despite studies demonstrating the beneficial effects of tight glycemic control on chronic complications of diabetes, clinicians are not particularly keen on aggressive insulin therapy, particularly in the early stages of the disease, and this is widely accepted in clinical practice. The unmet challenge of achieving tight glycemic control is due, in part, to the shortcomings of the available subcutaneous route of insulin administration and the fear of hypoglycemia. In addition to the practical limitations of multiple daily injections discussed above, the shortcomings of the commonly available subcutaneous route of insulin administration have resulted in the generally inadequate glycemic control believed to be associated with many of the chronic complications (comorbidities) associated with diabetes.

Hyperinsulinemia (elevated blood concentrations of insulin) can occur by the administration of insulin in a location (and manner) that is not consistent with the normal physiological route of delivery. Insulin circulates in blood as the free monomer, and its volume of distribution approximates the volume of extracellular fluid. Under fasting conditions, the concentration of insulin in portal blood is, e.g., about 2-4 ng/mL, whereas the systemic (peripheral) concentration of insulin is, e.g., about 0.5 ng/mL, in normal healthy humans, translating into, e.g., a 5:1 ratio. In human diabetics who receive insulin via subcutaneous injection, the ratio is changed to about 0.75:1. Thus, in such diabetic patients, the liver does not receive the necessary concentrations of insulin to adequately control blood glucose. Elevated systemic levels of insulin may lead to increased glucose uptake, glycogen synthesis, glycolysis, fatty acid synthesis, cortisol synthesis and triacylglycerol synthesis, leading to the expression of key genes that result in greater utilization of glucose.

In the field of insulin delivery, where multiple repeated administrations are required on a daily basis throughout the patient's life, it is desirable to create compositions of insulin that do not alter physiological clinical activity and that do not require injections. Oral delivery of insulin is a particularly desirable route of administration, for safety and convenience considerations, because it can minimize or eliminate the discomfort that often attends repeated hypodermic injections. It has been a significant unmet goal in the art to imitate normal insulin levels in the portal and systemic circulation via oral administration of insulin.

Oral delivery of insulin may have advantages beyond convenience, acceptance and compliance issues. Insulin absorbed in the gastrointestinal tract mimics the physiology of insulin secreted by the pancreas because both are released into the portal vein and carried directly to the liver before being delivered into the peripheral circulation. Absorption into the portal circulation maintains a peripheral-portal insulin gradient that regulates insulin secretion. In its first passage through the liver, roughly 60% of the insulin is retained and metabolized, thereby reducing the incidence of peripheral hyperinsulinemia, a factor linked to complications in diabetes. A not uncommon, and serious, complication of insulin treatment and other oral antidiabetic agents is hypoglycemia.

However, insulin exemplifies the problems confronted in the art in designing an effective oral drug delivery system for biological macromolecules. Insulin absorption in the gastrointestinal tract is prevented presumably by its molecular size and its susceptibility for enzymatic degradation. The physicochemical properties of insulin and its susceptibility to enzymatic digestion have precluded the design of a commercially viable oral or alternate delivery system.

Emisphere Technologies, Inc. has developed compositions of insulin that are orally administrable, e.g., absorbed from the gastrointestinal tract in adequate concentrations, such that the insulin is bioavailable and bioactive following oral administration and provide sufficient absorption and pharmacokinetic/pharmacodynamic properties to provide the desired therapeutic effect, i.e., cause a reduction of blood glucose, as disclosed in U.S. patent applications Ser. Nos. 10/237,138, 60/346,746, 60/347,312, 60/368,617, 60/374,979, 60/389,364, 60/438,195, 60/438,451, 60/438,444, 60/452,660 and 60/488,465, as well as in International Patent Application Publications Nos. WO 03/057170, WO 03/057650 and WO02/02509, all assigned to Emisphere Technologies, Inc., all of which are incorporated herein by reference.

The novel drug delivery technology of Emisphere Technologies, Inc. is based upon the design and synthesis of low molecular weight compounds called "delivery agents." When formulated with insulin, the delivery agent, which is in a preferred embodiment 4-CNAB (sodium N-[4-(4-chloro-2 hydroxybenzoyl)amino]butyrate) enables the gastrointestinal absorption of insulin. It is believed that the mechanism of this process is that 4-CNAB interacts with insulin non-covalently, creating more favorable physical-chemical properties for absorption. Once across the gastrointestinal wall, insulin disassociates rapidly from 4-CNAB and reverts to its normal, pharmacologically active state. 4-CNAB is not intended to possess any inherent pharmacological activity and serves only to increase the oral bioavailability of insulin by facilitating the transport of insulin across the gastrointestinal wall. The pharmacology of insulin is the desired therapeutic effect and is well characterized.

Whereas traditional subcutaneous insulin dosing shifts the point of entry of insulin into the circulation from the natural site (the portal vein) to the systemic circulation, the oral dosing method developed by Emisphere Technologies, Inc. mimics natural physiology, namely, the ratio of concentration of unmodified insulin in the portal circulation to that in the systemic circulation approaches the normal physiological ratio, e.g., from about 2:1 to about 6:1. The effect of this route of dosing is two fold. First, by targeting the liver directly, a greater control of glucose may be achieved. Various studies have shown that intraportal delivery of insulin can yield a comparable control of glucose at infusion rates lower than those required by peripheral administration. Because the insulin will undergo substantial (~50%) first-pass metabolism prior to entering the systemic circulation, a lower serum concentration and total exposure is achieved. This may, in turn, alleviate any detrimental effects of insulin on non-target tissues.

Insulin/4-CNAB capsules were evaluated by Emisphere Technologies, Inc. in a nonclinical program that included pharmacological screening, pharmacokinetic and metabolic profiles, and toxicity assessments in rats and monkeys. These studies in rats and monkeys showed that 4-CNAB is absorbed rapidly following oral administration.

Insulin/4-CNAB capsules were also evaluated by Emisphere Technologies, Inc. in clinical studies for the safety, pharmacokinetics, pharmacodynamics, and the effect of food on the absorption of insulin. In these studies, 4-CNAB was shown to enhance the gastrointestinal absorption of insulin following oral administration in diabetic patients and healthy subjects. Oral administration of Insulin/4-CNAB capsules resulted in rapid absorption of both insulin and 4-CNAB, and the insulin absorbed orally in combination with 4-CNAB was pharmacologically active, as demonstrated by a reduction of blood glucose in healthy and diabetic subjects and by a blunting of postprandial glucose excursion in diabetic patients. These studies suggest that oral administration of a formulation of insulin/4-CNAB is well-tolerated and reduces blood glucose concentrations in both healthy subjects and diabetic patients.

In normal physiology, first-phase insulin secretion takes place 5 to 20 minutes after the start of a meal, and this effect has a well-known impact on prandial glucose homeostasis. The loss of first-phase insulin secretion is a characteristic feature of Type 2 diabetic patients in the early stages of the disease, and it is also observed in prediabetic states, namely individuals with impaired glucose tolerance. In the absence of first-phase insulin secretion, the stimulatory effect of glucagon on gluconeogenesis is not suppressed and may contribute to the development of prandial hyperglycemia. In the basal state as well as in the prandial phase, plasma glucose concentrations are correlated with hepatic glucose output. Therefore, restoration of first-phase insulin secretion at the time of meal ingestion should suppress prandial hepatic glucose output and subsequently improve the blood glucose profile.

Several approaches have been undertaken to prove this hypothesis. However, the therapeutic regimens were either too dangerous for a long-term treatment (such as intravenous administration of regular human insulin) or pharmacologically unsuitable (fast-acting insulin analogues). Furthermore, restoration of first phase insulin response appears to be difficult in patients with a long-standing history of diabetes who have lost most or all of their endogenous insulin secretion capacity.

Currently, regular subcutaneously injected insulin is recommended to be dosed at 30 to 45 minutes prior to mealtime. As a result, diabetic patients and other insulin users must engage in considerable planning of their meals and of their insulin administrations relative to their meals. Unfortunately, intervening events that may take place between administration of insulin and ingestion of the meal may affect the anticipated glucose excursion. Furthermore, there is also the potential for hypoglycemia if the administered insulin provides a therapeutic effect over too great a time, e.g., after the rise in glucose levels that occur as a result of ingestion of the meal has already been lowered.

In addition, certain short acting insulin formulations, because of the speed with which the insulin provides a blood glucose lowering effect, may, between the time of administration of insulin and the time of ingestion of the meal, contribute to a lowering of blood glucose to a level that could range from subclinical hypoglycemia to more undesirable effects.

It is desirable to provide an oral insulin treatment for early phase and late phase diabetic patients, and for individuals with impaired glucose tolerance who have impaired first phase insulin secretion, which treatment can be administered orally at or shortly prior to mealtime and that has a short duration of action.

SUMMARY OF THE INVENTION

It is an object of the present invention to provide pharmaceutical compositions comprising insulin and a delivery agent for oral administration at or shortly prior to bedtime.

It is a further object of the present invention to provide useful pharmaceutical formulations of insulin for oral administration which are therapeutically and quickly effective.

It is an object of the present invention to provide compositions comprising insulin and a delivery agent for oral administration at or shortly prior to bedtime.

It is an object of the present invention to provide compositions for oral administration at or shortly prior to bedtime of insulin and a delivery agent that facilitates insulin transport in a therapeutically effective amount to the bloodstream for the treatment of diabetes, for the treatment of impaired glucose tolerance, for the purpose of achieving glucose homeostasis, for the treatment of early stage diabetes, for the treatment of late stage diabetes, and/or to serve as replacement therapy for type I diabetic patients.

It is a further object of the invention to provide methods for prophylactically sparing pancreatic beta cell function and for preventing beta cell death or dysfunction in a mammal that has impaired glucose tolerance or early stage diabetes.

It is a further object of the invention to provide methods for long term protection of a mammal from developing overt or insulin dependent diabetes or for delaying the onset of overt or insulin dependent diabetes in a mammal, the mammal having impaired glucose tolerance or early stage diabetes mellitus.

In accordance with the above objects and others, the invention is directed in part to a method of treatment of diabetes in mammals, comprising orally administering one or more unit doses of the dosage forms described above and in further sections of the present specification at or shortly prior to bedtime.

Mammals includes but is not limited to rodents, aquatic mammals, domestic animals such as dogs and cats, farm animals such as sheep, pigs, cows and horses, and humans. Preferably, the mammal is a human.

The invention is further directed in part to a method of treatment of impaired glucose tolerance, early stage diabetes and late stage diabetes in mammals, and of achieving glucose homeostasis, comprising administering one or more unit doses of the dosage forms described in the present specification at or shortly prior to bedtime. Preferably, the oral insulin formulation is administered to such patients on a chronic basis, e.g., for at least about 2 weeks, and can be administered for the life of the patient.

The present invention is also directed in part to a method of treating diabetes and reducing the incidence of systemic hyperinsulinemia associated with chronic dosing of insulin, comprising orally administering to a diabetic patient at or shortly prior to bedtime a dose of insulin and a delivery agent that facilitates the absorption of the dose of insulin from the gastrointestinal tract to provide a therapeutically effective reduction and/or control in blood glucose and a mean systemic blood insulin concentration of the diabetic patient that is reduced relative to the mean systemic blood insulin concentration provided by subcutaneous injection of insulin in an amount effective to achieve equivalent reduction and/or control in a population of diabetic patients. Preferably, the oral insulin formulation is administered to such patients on a chronic basis, e.g., for at least about 2 weeks, and can be administered for the life of the patient. The mean values of insulin concentration determination obtained in patients who have been administered subcutaneous insulin are well known to those skilled in the art.

The present invention is further directed to a method for prophylactically sparing beta cell function in a mammal which has impaired glucose tolerance or early stage diabetes mellitus, comprising administering an orally effective dose of a pharmaceutical formulation comprising insulin (as described herein) at nighttime, e.g., at or shortly prior to bedtime. Preferably, the oral insulin formulation is administered to such patients on a chronic basis, e.g., for at least about 2 weeks, and can be administered for the life of the patient.

The present invention is further directed to a method for preventing beta cell death or dysfunction in a mammal which has impaired glucose tolerance or early stage diabetes mellitus, comprising administering an orally effective dose of a pharmaceutical formulation comprising insulin at nighttime. Preferably, the oral insulin formulation is administered to such patients at or shortly prior to bedtime on a chronic basis, e.g., for at least about 2 weeks.

The present invention is further directed to a method for long-term protection of a mammal which has impaired glucose tolerance or early stage diabetes mellitus from developing overt or insulin dependent diabetes, comprising administering an orally effective dose of a pharmaceutical formulation comprising insulin at nighttime. Preferably, the oral insulin formulation is administered to such patients at or shortly prior to bedtime on a chronic basis, e.g., for at least about 2 weeks.

The present invention is further directed to a method for delaying the onset of overt or insulin dependent diabetes in a mammal which has impaired glucose tolerance or early stage diabetes mellitus, comprising administering an orally effective dose of a pharmaceutical formulation comprising insulin at nighttime. Preferably, the oral insulin formulation is administered to such patients at or shortly prior to bedtime on a chronic basis, e.g., for at least about 2 weeks.

The invention is further directed to a method of providing a therapeutically effective orally administrable unit dose of unmodified insulin, comprising combining from about 2 to about 23 mg of unmodified insulin with from about 100 to about 600 mg of a pharmaceutically acceptable delivery agent which facilitates absorption of said insulin from the gastrointestinal tract, and orally administering said unit dose to a diabetic patient at or shortly prior to bedtime to provide a therapeutic effect. In preferred embodiments, the total weight of the unit dose is from about 102 mg to about 800 mg.

In certain embodiments, the method comprises the following steps: contacting insulin with said delivery agent, and thereafter orally administering the pharmaceutical composition to the patient at or shortly prior to bedtime. Alternatively, the method comprises administering the insulin and the delivery agent in such a manner that the insulin and delivery agent contact each other in-vivo (e.g., in the stomach), such that the delivery agent is available to facilitate absorption of the insulin through the gastrointestinal mucosa and into the portal vein, the normal physiologic route.

For the purposes of the present specification, the phrase administered "at nighttime" or "at or shortly before bedtime" means administered less than about 3 hours, preferably les than about 2 hours and more preferably less than about 1 hour prior to a prolonged period of sleep, or relative physical and/or mental inactivity, and fast, e.g., overnight. Whereas overnight typically means from the late night (p.m.) hours to the early morning (a.m.) hours, it could mean any period of a sleep-wake cycle during which a person obtains his/her necessary period of sleep. For the purposes of the present specification, administration should also occur at least about one hour, preferably at least about 1.5 hours, more preferably at least about 2 hours and still more preferably at least about 2 to about 3 hours after the last meal of the day.

In accordance with the above objects and others, the invention is directed in part to an oral solid dosage form comprising a dose of unmodified insulin that, when administered at or shortly before bedtime, achieves a maximum control of post prandial blood glucose concentration in diabetic patients within one hour post-administration.

In accordance with the above objects and others, the invention is directed in part to an oral solid dosage form comprising a dose of unmodified insulin that achieves a reduction in blood glucose concentration in diabetic patients comparable to a subcutaneous insulin injection in those patients, while providing a lower (e.g., 20% or greater) totals dose of insulin in the peripheral blood circulation under acute, sub-acute and chronic conditions as compared to the peripheral blood insulin concentration obtained via the subcutaneous injection.

The invention is also directed in part to an oral solid dosage form comprising a dose of unmodified insulin that achieves a therapeutically effective reduction in blood glucose after oral administration to a diabetic patient, and which maintains a physiological (portal/peripheral) gradient, and in certain embodiments provides a ratio of portal vein insulin concentration to peripheral blood insulin concentration from about 2.5:1 to about 6:1, and preferably from about 4:1 to about 5:1.

The invention is further directed in part to an oral dosage form comprising a dose of unmodified insulin that achieves a therapeutically effective reduction in blood glucose after oral administration to diabetic patients, the oral solid dosage form providing an insulin $t_{max}$ at a time point from about 0.25 to about 1.5 hours after oral administration to said patients, at least about 80% of the blood glucose concentration reduction caused by said dose of insulin occurring within about 2 hours after oral administration of said dosage form.

In preferred embodiments of the oral dosage forms of the invention described above, the oral dosage form is solid, such as a gelatin capsule or a tablet.

In certain preferred embodiments, the dose of unmodified insulin contained in the dosage form is from about 50 Units to about 600 Units (from about 2 to about 23 mg), preferably from about 100 Units (3.8 mg) to about 450 Units (15.3 mg) insulin, more preferably from about 200 Units (7.66 mg) to about 350 Units (13.4 mg), and still more preferably about 300 Units (11.5 mg), based on the accepted conversion of factor of 26.11 Units per mg.

In certain preferred embodiments, the dosage forms of the invention provide a $t_{max}$ for insulin at about 0.1 to about 1.5 hours, and more preferably by about 0.25 to about 0.5 hours, after oral administration. In certain preferred embodiments, the $t_{max}$ for insulin occurs at less than about 100 minutes after oral administration of the composition, preferably at less than about 45 minutes, more preferably at less than about 40 minutes, and still more preferably at about 22 minutes after oral administration of the composition.

In certain preferred embodiments, the composition provides a $t_{max}$ for maximum control of glucose excursion at about 0.25 to about 1.5 hours, more preferably at about 0.75 to about 1.25 hours, after oral administration. In certain preferred embodiments, the $t_{max}$ for glucose control occurs preferably at less than about 120 minutes, more preferably at less than about 80 minutes, and still more preferably at about 45 minutes to about 60 minutes, after oral administration of the composition.

In certain preferred embodiments of the invention, the dosage forms begin delivering insulin into the portal circulation (via absorption through the mucosa of the stomach) to achieve peak levels within about 30 minutes or less.

In certain embodiments of the dosage forms described above, in the absence of a delivery agent, the dose of unmodified insulin is not adequately absorbed from the gastrointestinal tract when administered orally to render a desired effect. In certain preferred embodiments, in the absence of a delivery agent, the dose of insulin is not sufficiently absorbed when orally administered to a patient to provide a desirable therapeutic effect but said dose provides a desirable therapeutic effect when administered to said patient by another route of administration. The invention in such embodiments is further directed to an oral dosage form comprising a dose of unmodified insulin together with a pharmaceutically acceptable delivery agent in an amount effective to facilitate the absorption of said insulin, such that a therapeutically effective amount of said dose of insulin is absorbed from the gastrointestinal tract of diabetic patients.

In certain preferred embodiments, the pharmaceutical composition comprises from about 1 mg to about 800 mg of said delivery agent, preferably about 50 to about 600, more preferably from about 100 to about 400, most preferably about 200. In certain embodiments, the composition provides a peak plasma delivery agent concentration $C_{max}$ from about 1,000 and about 150,000 ng/ml, and a $t_{max}$ at about 0.25 to about 1.5 hours, and more preferably by about 0.25 to about 0.75 hours, most preferably 0.5 hours, after oral administration.

For purposes of the present invention, a preferred delivery agent is identified via chemical nomenclature as 4-[(4-chloro, 2-hydroxybenzoyl)amino]butanoic acid. In certain preferred embodiments, the delivery agent is a sodium salt, preferably monosodium salt. Alternatively, the same compound is identified by the alternative nomenclature monosodium N-(4-chlorosalicyloyl)-4-aminobutyrate, or by the short name "4-CNAB".

The following terms will be used throughout the application as defined below:

Diabetic patient—refers to a mammal with a form of diabetes.

IGT—means impaired glucose tolerance.

Diabetes or Diabetes Mellitus—is deemed to encompass type 1 and type 2 diabetes mellitus, unless specifically specified otherwise.

Delivery agent—refers to carrier compounds or carrier molecules that are effective in the oral delivery of therapeutic agents, and may be used interchangeably with "carrier".

Therapeutically effective amount of insulin—refers to an amount of insulin included in the dosage forms of the invention which is sufficient to achieve a clinically relevant control of blood glucose concentrations in a human diabetic patient either in the fasting state or in the fed state effective, during the dosing interval.

Effective amount of delivery agent—an amount of the delivery agent that promotes the absorption of a therapeutically effective amount of the drug from the gastrointestinal tract.

Organic solvents—refers to any solvent of non-aqueous origin, including liquid polymers and mixtures thereof. Organic solvents suitable for the present invention include: acetone, methyl alcohol, methyl isobutyl ketone, chloroform, 1-propanol, isopropanol, 2-propanol, acetonitrile, 1-butanol, 2-butanol, ethyl alcohol, cyclohexane, dioxane, ethyl acetate, dimethylformamide, dichloroethane, hexane, isooctane, methylene chloride, tert-butyl alchohol, toluene, carbon tetrachloride, or combinations thereof.

Peptide—refers to a polypeptide of small to intermediate molecular weight, usually 2 or more amino acid residues and frequently but not necessarily representing a fragment of a larger protein.

Protein—refers to a complex high polymer containing carbon, hydrogen, oxygen, nitrogen and usually sulfur and composed of chains of amino acids connected by peptide linkages. Proteins in this application refer to glycoproteins, antibodies, non-enzyme proteins, enzymes, hormones and sub-units of proteins, such as peptides. The molecular weight range for proteins includes peptides of 1000 Daltons to glycoproteins of 600 to 1000 kiloDaltons.

Reconstitution—refers to dissolution of compositions or compositions in an appropriate buffer or pharmaceutical composition.

Unit-Dose Forms—refers to physically discrete units suitable for human and animal subjects and packaged individually as is known in the art. It is contemplated for purposes of the present invention that dosage forms of the present invention comprising therapeutically effective amounts of insulin may include one or more unit doses (e.g., tablets, capsules, powders, semisolids (e.g. gelcaps or films), liquids for oral admisistration, ampoules or vials for injection, loaded syringes) to achieve the therapeutic effect. It is further contemplated for the purposes of the present invention one preferred embodiment of the dosage form is an oral dosage form.

Unmodified insulin—refers to insulin prepared in any pharmaceutically acceptable manner or from any pharmaceutically acceptable source which is not conjugated with an oligomer such as that described in U.S. Pat. No. 6,309,633 and/or which not has been subjected to amphiphilic modification such as that described in U.S. Pat. Nos. 5,359,030; 5,438,040; and/or 5,681,811, which patents are hereby incorporated by reference in their entireties.

The term "meal" means a standard, ADA and/or a mixed meal.

The term "mean", when preceding a pharmacokinetic value (e.g., mean $t_{max}$), represents the arithmetic mean value of the pharmacokinetic value unless otherwise specified.

The term "mean baseline level" means the measurement, calculation or level of a certain value that is used as a basis for comparison, which is the mean value over a statistically significant number of subjects, e.g., across a single clinical study or a combination of more than one clinical study.

The term "$C_{max}$" as used herein is the highest plasma concentration of the drug observed within the dosing interval.

The term "$t_{max}$" as used herein is the time post-dose at which $C_{max}$ is observed.

The term "AUC" as used herein means area under the plasma concentration-time curve, as calculated by the trapezoidal rule over the complete sample collection interval.

The term "multiple dose" means that the human patient has received at least two doses of the drug composition in accordance with the dosing interval for that composition.

The term "single dose" means that the human patient has received a single dose of the drug composition and the drug plasma concentration has not achieved steady state. Unless specifically designated as "single dose" or at "steady-state", the pharmacokinetic parameters disclosed and claimed herein encompass both single dose and steady-state conditions.

The term "Bioavailability" as used herein means the degree or ratio (%) to which a drug or agent is absorbed or otherwise available to the treatment site in the body. This is calculated by the formula $$\text{Relative Bioavailability (\%)} = \frac{\text{Dose } SC}{\text{Dose Oral}} \times \frac{AUC \text{ Oral}}{AUC \text{ } SC} \times 100$$

The term "Biopotency" as used herein means the degree or ratio (%) to which a drug or agent is effective to the treatment site in the body. This is calculated by the formula $$\text{Relative Biopotency (\%)} = \frac{\text{Dose } SC}{\text{Dose Oral}} \times \frac{AUC \text{ Oral}}{AUC \text{ } SC} \times 100$$

As used herein and in the appended claims, the singular forms "a," "an," and "the," include plural referents unless the context clearly indicates otherwise. Thus, for example, reference to "a molecule" includes one or more of such molecules, "a reagent" includes one or more of such different reagents, reference to "an antibody" includes one or more of such different antibodies, and reference to "the method" includes reference to equivalent steps and methods known to those of ordinary skill in the art that could be modified or substituted for the methods described herein.

Unless defined otherwise, all technical and scientific terms used herein have the same meaning as commonly understood by one of ordinary skill in the art to which the invention belongs. Although any methods, compositions, reagents, cells, similar or equivalent to those described herein can be used in the practice or testing of the invention, the preferred methods and materials are described herein. All publications mentioned herein are incorporated herein, including all figures, graphs, equations, illustrations, and drawings, to describe and disclose specific information for which the reference was cited in connection with.

The publications discussed above are provided solely for their disclosure before the filing date of the present application. Nothing herein is to be construed as an admission that the invention is not entitled to antedate such disclosure by virtue of prior invention. Throughout this description, the preferred embodiment and examples shown should be considered as exemplars, rather than as limitations on the present invention.

BRIEF DESCRIPTION OF THE DRAWINGS

FIG. 1 is a table of data (blood glucose, insulin and C-peptide) collected in the morning after nighttime dosing of insulin and 4-CNAB for each subject compared to that subject's own baseline levels.

DETAILED DESCRIPTION

Figures 2, 3:
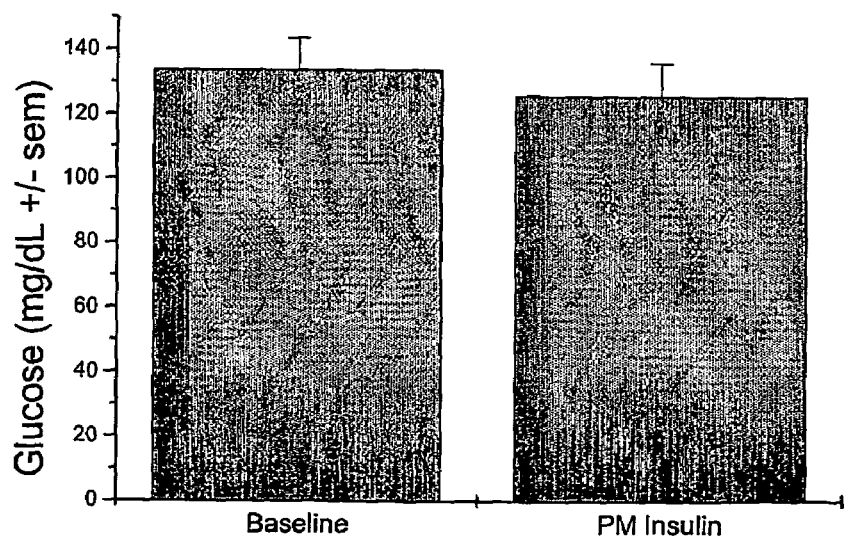
FIG. 2 is a table of data (insulin and C-peptide) collected at night prior to nighttime dosing of insulin and 4-CNAB for each subject.
FIG. 3 is a bar graph showing the effect of nighttime dosing of insulin and 4-CNAB on blood glucose concentration.

The invention further provides a method of treatment of diabetes, impaired glucose tolerance, early stage diabetes, and late stage diabetes in animals, preferably humans, and a method of achieving glucose homeostasis, comprising administering one or more unit doses of the dosage forms described in the present specification at or shortly before bedtime, preferably on a chronic basis.

The invention further provides a method for treating animals, preferably humans with an oral dosage form of a pharmaceutical composition that includes: insulin or a pharmaceutically acceptable salt thereof and an effective amount of a delivery agent or a pharmaceutically acceptable salt thereof that renders insulin orally absorbed (i.e., bioavailable), by administering said composition to said animals, preferably humans on a chronic basis at or shortly before bedtime.

The invention further provides a method of treating diabetes and/or reducing the incidence of systemic hyperinsulinemia associated with chronic dosing of insulin, comprising orally administering to a diabetic patient at or shortly before bedtime, preferably on a chronic basis, a dose of insulin and a delivery agent that facilitates the absorption of the dose of insulin from the gastrointestinal tract.

The present invention is further directed to method for prophylactically sparing beta cell function in a mammal which has impaired glucose tolerance or early stage diabetes mellitus, comprising administering an orally effective dose of a pharmaceutical formulation comprising insulin (as described herein) at or shortly prior to bedtime on a chronic basis, e.g., for at least about 2 weeks, or for the life of the patient.

The present invention is further directed to a method for preventing beta cell death or dysfunction in a mammal which has impaired glucose tolerance or early stage diabetes mellitus, comprising administering an orally effective dose of a pharmaceutical formulation comprising insulin at or shortly prior to bedtime on a chronic basis, e.g., for at least about 2 weeks.

The present invention is further directed to a method for long-term protection of a mammal which has impaired glucose tolerance or early stage diabetes mellitus from developing overt or insulin dependent diabetes, comprising administering an orally effective dose of a pharmaceutical formulation comprising insulin at or shortly prior to bedtime on a chronic basis, e.g., for at least about 2 weeks.

The present invention is further directed to a method for delaying the onset of overt or insulin dependent diabetes in a mammal which has impaired glucose tolerance or early stage diabetes mellitus, comprising administering an orally effective dose of a pharmaceutical formulation comprising insulin at or shortly prior to bedtime on a chronic basis, e.g., for at least about 2 weeks.

In general, the present invention provides a method of administering insulin and pharmaceutical compositions useful for administering insulin such that the insulin is bioavailable and biopotent. The delivery agent enables insulin to be orally absorbable through the mucosa of the stomach and facilitates the absorption of insulin administered therewith (either in the same dosage form, or simultaneously therewith), or sequentially (in either order, as long as both the delivery agent and insulin are administered within a time period which provides both in the same location, e.g., the stomach, at the same time). Following oral administration of the pharmaceutical compositions of the present invention, the delivery agent passes though the mucosal barriers of the gastrointestinal tract and is absorbed into the blood stream where it can be detected in the plasma and/or blood of subjects. The level of delivery agent in the bloodstream as measured in the plasma and/or blood is dose-dependent.

One preferred pharmaceutical composition of the inventions comprises a combination of insulin and a delivery agent in a suitable pharmaceutical carrier or excipient as understood by practitioners in the art. It is preferred that the dosage form of the pharmaceutical composition of the present invention is a solid dosage form, such as a gelatin capsule or a tablet.

By virtue of the present invention, the ratio of portal (unmodified) insulin concentration to systemic (unmodified) insulin concentration approaches in human diabetic patients approaches that which is obtained in normal healthy humans. The chronic administration of oral dosage forms of the present invention result in a higher portal insulin concentration and lower systemic insulin concentration over time than that obtained with an equi-effective dose of insulin administered subcutaneously (i.e., which provide similar control of blood glucose levels). Transient peaks in insulin levels that may occur by virtue of the oral administration of insulin in accordance with the present invention is not believed to be associated with vascular diseases.

As used herein, "insulin" refers to insulin from a variety of sources. Naturally occurring insulin and structurally similar bioactive equivalents (insulin analogues including short acting and analogues with protracted action) can be used. Insulin useful in the invention can be may be obtained by isolating it from natural source, such as different species of mammal. For example, animal insulin preparations extracted from bovine or porcine pancreas can be used. Insulin analogues, fragments, mimetics or polyethylene glycol (PEG)-modified derivatives of these compounds, derivatives and bioequivalents thereof can also be used with the invention.

The insulin used in the present invention may be obtained by chemically synthesizing it using protein chemistry techniques such as peptide synthesis, or by using the techniques of molecular biology to produce recombinant insulin in bacteria or eukaryotic cells. The physical form of insulin may include crystalline and/or amorphous solid forms. In addition, dissolved insulin may be used. Other suitable forms of insulin, including, but not limited to, synthetic forms of insulin, are described in U.S. Pat. Nos. 4,421,685, 5,474,978, and 5,534,488, the disclosure of each of which is hereby incorporated by reference in its entirety.

The most preferred insulin useful in the pharmaceutical compositions and methods of the present invention is human recombinant insulin optionally having counter ions including zinc, sodium, calcium and ammonium or any combination thereof. Human recombinant insulin can be prepared using genetic engineering techniques that are well known in the art. Recombinant insulin can be produced in bacteria or eukaryotic cells. Functional equivalents of human recombinant insulin are also useful in the invention. Recombinant human insulin can be obtained from a variety of commercial sources. For example, insulin (Zinc, human recombinant) can be purchased from Calbiochem (San Diego, Calif.). Alternatively, human recombinant Zinc-Insulin Crystals: Proinsulin Derived (Recombinant DNA Origin) USP Quality can be obtained from Eli Lilly and Company (Indianapolis, Ind.). All such forms of insulin, including insulin analogues (including but not limited to Insulin Lispro, Insulin Aspart, Insulin Glargine, and Insulin Detemir) are deemed for the purposes of this specification and the appended claims are considered to be encompassed by the term "insulin." The present invention also provides compositions of recombinant human zinc insulin and a delivery agent as a drug for oral administration of insulin in humans.

In other preferred embodiments of the invention, the insulin is a modified insulin, such as that conjugated with an oligomer such as that described in U.S. Pat. No. 6,309,633 and/or which not has been subjected to amphiphilic modification such as that described in U.S. Pat. Nos. 5,359,030; 5,438,040; and/or 5,681,811. The conjugated (modified) insulin may be incorporated into the oral formulations of the present invention in addition to or in the absence of any of the types of insulin described above, as well as with other insulin analogues. In such embodiments, the oral formulations include the modified insulin either with or without a pharmaceutically acceptable delivery agent that facilitates absorption of said insulin from the gastrointestinal tract.

It is preferable that the oral dosage form comprise a therapeutically effective amount of unmodified insulin, i.e., a pharmacologically or biologically effective amount, or an amount effective to accomplish the purpose of insulin. The dose of insulin administered should preferably be in such an amount that, upon oral administration, it results in a measurable and statistically significant reduction in blood glucose levels in normal healthy human subjects.

However, the amount can be less than a pharmacologically or biologically effective amount when the composition is used in a dosage unit form, such as a tablet, because the dosage unit form may contain a multiplicity of delivery agent/biologically or chemically active agent compositions or may contain a divided pharmacologically or biologically effective amount. The total effective amounts can then be administered in cumulative units containing, in total, pharmacologically, biologically or chemically active amounts of biologically or pharmacologically active agent.

The total amount of insulin to be used can be determined by those skilled in the art. The amount of insulin is an amount effective to accomplish the purpose of the particular active agent. The amount in the composition is a therapeutically effective dose, i.e., a pharmacologically or biologically effective amount. However, the amount can be less than a pharmacologically or biologically effective amount when the composition is used in a dosage unit form, such as a capsule, a tablet or a liquid, because the dosage unit form may contain a multiplicity of delivery agent/biologically or chemically active agent compositions or may contain a divided pharmacologically or biologically effective amount. The total effective amounts can then be administered in cumulative units containing, in total, pharmacologically or biologically or chemically active amounts of biologically or pharmacologically active agent.

However, it has surprisingly been found that the use of the presently disclosed delivery agents provides extremely efficient delivery of insulin. Preferred insulin doses, when dosed in combination with the delivery agents described herein, are about 50 to about 600 insulin Units USP (from about 2 to about 23 mg), preferably from about 100 Units (3.8 mg) to about 450 Units (15.3 mg), more preferably from about 200 Units (7.66 mg) to about 350 Units (13.4 mg), and still more preferably about 300 Units (11.5 mg), based on the accepted conversion of factor of 26.11 Units per mg.

Insulin entry into the bloodstream produces a decrease in plasma glucose levels. Therefore, oral absorption of insulin may be verified by observing the effect on a subject's blood sugar following oral administration of the composition. In a preferred embodiment of the invention, the oral dosage forms of the invention facilitate the oral delivery of insulin, and after insulin is absorbed into the bloodstream, the composition produces a maximal decrease in blood glucose in treated patients from about 20 to about 60 minutes after oral administration. In another embodiment of the present invention, the pharmaceutical composition produces a maximal decrease in blood glucose in treated patients from about 30 to about 50 minutes post oral administration. More particularly, the pharmaceutical composition produces a maximal decrease in blood glucose in treated patients at about 40 minutes after oral administration.

The magnitude of the decrease in blood glucose produced by insulin absorbed into the bloodstream following entry into the gastrointestinal tract varies with the dose of insulin. In certain embodiments of the invention, human diabetic patients show a maximal decrease in blood glucose by at least 10% within one hour post oral administration. In another embodiment, human diabetic patients show a maximal decrease in blood glucose by at least 20% within one hour post oral administration, alternatively, at least 30% within one hour post oral administration.

Normal levels of blood glucose vary somewhat throughout the day and in relation to the time since the last meal. One goal of the present invention is to provide oral compositions of insulin that facilitate achieving close to normal levels of blood glucose throughout the 24-hour daily cycle. In a preferred embodiment of the invention, wherein the pharmaceutical composition includes insulin or an insulin analog as the active agent and a delivery agent in an amount effective to achieve a fasting blood glucose concentration from about 90 to about 110 mg/dl. In another preferred embodiment of the invention, wherein the pharmaceutical composition includes insulin or an insulin analog as the active agent and a delivery agent in an amount effective to achieve a fasting blood glucose concentration from about 95 to about 105 mg/dl, more preferably, the subject manifests fasting blood glucose concentrations at about 100 mg/dl.

In the time after a meal is consumed, blood glucose concentration rises in response to digestion and absorption into the bloodstream of carbohydrates derived from the food eaten. The present invention provides oral compositions of insulin that prevent or control very high levels of blood glucose from being reached and/or sustained. More particularly, the present invention provides compositions which facilitate achieving normal levels of blood glucose after a meal has been consumed, i.e., post-prandial. In a preferred embodiment of the invention, the pharmaceutical composition includes insulin as the active agent and a delivery agent in an amount effective to achieve a post-prandial blood glucose concentration from about 130 to about 170 mg/dl. In another preferred embodiment of the invention, the pharmaceutical composition includes insulin or an insulin analog as the active agent and a delivery agent in an amount effective to achieve a post-prandial blood glucose concentration from about 140 to about 160 mg/dl, more preferably, the subject manifests fasting blood glucose concentrations at less than about 160 mg/dl.

The present invention provides pharmaceutical compositions for oral administration which includes insulin or an insulin analog as the active agent and a delivery agent in an amount effective to achieve pre-prandial (before a meal is consumed) blood glucose concentration from about 95 to about 125 mg/dl. In a preferred embodiment, the present invention provides pharmaceutical compositions for oral administration which includes insulin or an insulin analog as the active agent and a delivery agent in an amount effective to achieve pre-prandial blood glucose concentration from about 100 to about 120 mg/dl.

The present invention provides pharmaceutical compositions for oral administration which include insulin as the active agent and a delivery agent in an amount effective to achieve blood glucose concentrations within the normal range during the evening period from about 70 to about 120 mg/dl. In a preferred embodiment, the present invention provides pharmaceutical compositions for oral administration which include insulin or an insulin analog as the active agent and a delivery agent in an amount effective to achieve blood glucose concentrations at 3 AM from about 80 to about 120 mg/dl.

In certain preferred embodiments, the methods and pharmaceutical compositions provide the pharmacokinetic parameters set forth in U.S. Provisional Applications Nos. 60/346,746 and 60/347,312, the disclosure of each of which is incorporated herein by reference.

The amount of delivery agent necessary to adequately deliver insulin into the blood stream of a subject needing the therapeutic effect of insulin can vary depending on one or more of the following; chemical structure of the particular delivery agent; the nature and extent of interaction of insulin and the delivery agent; the nature of the unit dose, i.e., solid, liquid, tablet, capsule, suspension; the concentration of delivery agent in the GI tract, the feeding state of the subject, the diet of the subject, the heath of the subject and the ratio of delivery agent to insulin.

In preferred embodiments, the oral dosage forms of the present invention comprise a mixture of insulin and a delivery agent, e.g., monosodium N-(4-chlorosalicyloyl)-4-aminobutyrate (4-CNAB), a novel compound discovered by Emisphere Technologies, Inc., or separately containing insulin and the delivery agent.

In further embodiments of the present invention, the oral dosage forms described herein are orally administered as described herein in combination with an additional therapy to treat diabetes, impaired glucose tolerance, or to achieve glucose homeostasis, said additional therapy comprising, for example, an additional drug such as sulfonylurea, a biguanide, an alpha-glucosidase, insulin delivered via a different pathway (e.g., parenteral insulin), and/or an insulin sensitizer.

In further embodiments of the invention, the oral dosage forms described herein reduce the likelihood of hypoglycemic events, mainly because of two reasons. First, one cannot hyperinsulinize the liver, because even under hyperinsulinemia the liver uptake of glucose will be unchanged. Unlike the peripheral tissue, the liver will only cease stimulating the pancreas to produce endogenous insulin, and the liver will not sequester additional glucose. In addition, (b) the short peak of insulin (e.g., as shown in the appended examples) shows that, even if insulin were to reach high peripheral levels, the peak drops precipitously.

The effect of absorption of insulin is manifested in human patients treated with the pharmaceutical compositions of the present invention by observing reductions in C-peptide concentration following oral treatment. For example, in one embodiment of the invention, the pharmaceutical composition comprises insulin as the active agent and the compound 4-CNAB as a delivery agent to facilitate the oral delivery of insulin, and, after insulin is absorbed into the bloodstream, the composition produces a maximal decrease in C-peptide concentration in treated patients from about 80 and about 120 minutes post oral administration. More particularly, the composition produces a maximal decrease in C-peptide concentration in treated patients from about 90 and about 110 minutes post oral administration.

Absorption of insulin can be detected in subjects treated with the pharmaceutical compositions of the present invention by monitoring the plasma levels of insulin after treatment. The time it takes for an active agent to reach a peak in the bloodstream ($t_{max}$) may depend on many factors such as the following: the nature of the unit dose, i.e., solid, liquid, tablet, capsule, suspension; the concentration of active agent and delivery agent in the GI tract; the feeding state of the subject; the diet of the subject; the health of the subject and the ratio of active agent to the delivery agent. In a preferred embodiment of the invention, wherein the pharmaceutical composition includes the compound 4-CNAB as the delivery agent and insulin as the active agent, the composition provides a peak plasma insulin concentration from about 0.1 to about 1 hour after oral administration. In another embodiment, the composition provides a peak plasma insulin concentration from about 0.2 to about 0.6 hours after oral administration. In a preferred embodiment, the composition provides a peak plasma insulin concentration from about 0.3 to about 0.4 hours after oral administration. In another embodiment, the composition provides a peak plasma insulin concentration within about 1 hour after oral administration. In certain preferred embodiments of the invention, the pharmaceutical composition comprises insulin as the active agent and the compound 4-CNAB as a delivery agent to facilitate the oral delivery of insulin, and after insulin is absorbed into the, bloodstream, the plasma insulin levels in treated patients peak at about 20 minutes post oral administration with a second peak at about 105 minutes.

In other preferred embodiments, the delivery agents used in the invention have the following structure:

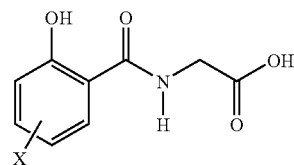

wherein X is one or more of hydrogen, halogen, hydroxyl or $C_1$-$C_3$ alkoxy, and R is substituted or unsubstituted $C_1$-$C_3$ alkylene, substituted or unsubstituted $C_1$-$C_3$ alkenylene.

In certain preferred embodiments, the delivery agents of the invention preferably have the following structure:

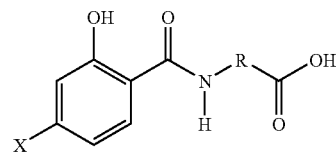

wherein X is halogen, and R is substituted or unsubstituted $C_1$-$C_3$ alkylene, substituted or unsubstituted $C_1$-$C_3$ alkenylene.

In a preferred embodiment of the present invention, the pharmaceutical composition includes a delivery agent wherein X is chlorine and R is $C_3$ alkylene. In another preferred embodiment of the present invention, the pharmaceutical composition includes the compound 4-[(4-chloro, 2-hydroxybenzoyl)amino]butanoic acid as a delivery agent for the oral delivery of insulin, preferably the monosodium salt thereof.

The delivery agents may be in the form of the carboxylic acid or salts thereof. Suitable salts include, but are not limited to, organic and inorganic salts, for example alkali-metal salts, such as sodium, potassium and lithium; alkaline-earth metal salts, such as magnesium, calcium or barium; ammonium salts; basic amino acids, such as lysine or arginine; and organic amines, such as dimethylamine or pyridine. Preferably, the salts are sodium salts. The salts may be mono- or multi-valent salts, such as monosodium salts and di-sodium salts. The salts may also be solvates, including ethanol solvates, and hydrates.

Other suitable delivery agents that can be used in the present invention include those delivery agents described U.S. Pat. Nos. 5,650,386, 5,773,647, 5,776,888, 5,804,688, 5,866,536, 5,876,710, 5,879,681, 5,939,381, 5,955,503, 5,965,121,5,989,539, 5,990,166, 6,001,347, 6,051,561, 6,060,513, 6,090,958, 6,100,298, 5,766,633, 5,643,957, 5,863,944, 6,071,510 and 6,358,504, the disclosure of each of which is incorporated herein by reference. Additional suitable delivery agents are also described in International Publications Nos. WO 94/23767, WO 95/11690, WO 95/28920, WO 95/28838, WO 96/10396, WO96/09813, WO 96/12473, WO 96/12475, WO 96/30036, WO 96/33699, WO 97/31938, WO 97/36480, WO 98/25589, WO 98/34632, WO 98/49135, WO 98/25589, WO 99/16427, WO 00/47188, WO 00/07979, WO 00/59863, WO 00/06534, WO 00/40203, WO 00/46182, WO 00/48589, WO 00/50386, WO 00/59480, WO 01/34114, WO 01/21073, WO 01/41985, WO 01/32130, WO 01/32596, WO 01/44199, WO 01/51454, WO 01/25704, WO 01/25679, WO 01/70219, WO 01/92206, WO 02/02509, WO 02/15959, WO 02/16309, WO 02/070438, WO 02/02509, WO 02/20466, WO02/100338, WO 02/19969 and WO 03/026582, and International Patent Applications Nos. PCT/US02/06610, PCT/US02/06295, and PCT/US02/36552 the disclosure of each of which is incorporated herein by reference.

Salts of the delivery agent compounds of the present invention may be prepared by methods known in the art. For example, sodium salts may be prepared by dissolving the delivery agent compound in ethanol and adding aqueous sodium hydroxide.

The compounds described herein may be derived from amino acids and can be readily prepared from amino acids by methods known by those with skill in the art based upon the present disclosure and the methods described in International Publications Nos. WO 96/30036, WO 97/36480, WO 98/34632 and WO 00/07979, and in U.S. Pat. Nos. 5,643,957 and 5,650,386, the disclosure of each of which is incorporated herein by reference. For example, the compounds may be prepared by reacting the single amino acid with the appropriate acylating or amine-modifying agent, which reacts with a free amino moiety present in the amino acid to form amides. Protecting groups may be used to avoid unwanted side reactions as would be known to those skilled in the art.

The delivery agents may also be prepared by the methods of International Publications Nos. WO 02/02509 and WO 03/057650), the disclosures of which is incorporated herein by reference. The delivery agents may also be prepared by alkylation of the appropriate salicylamide according to the methods of International Publication No. WO 00/46182, the disclosure of which is incorporated herein by reference. The salicylamide may be prepared from salicylic acid via the ester by reaction with sulfuric acid and ammonia.

In addition, poly amino acids and peptides comprising one or more of these compounds may be used. An amino acid is any carboxylic acid having at least one free amine group and includes naturally occurring and synthetic amino acids. Poly amino acids are either peptides (which are two or more amino acids joined by a peptide bond) or are two or more amino acids linked by a bond formed by other groups which can be linked by, e.g., an ester or an anhydride linkage. Peptides can vary in length from dipeptides with two amino acids to polypeptides with several hundred amino acids.

The delivery agent compound may be purified by recrystallization or by fractionation on one or more solid chromatographic supports, alone or linked in tandem. Suitable recrystallization solvent systems include, but are not limited to, ethanol, water, heptane, ethyl acetate, acetonitrile, methanol and tetrahydrofuran and mixtures thereof. Fractionation may be performed on a suitable chromatographic support such as alumina, using methanol/n-propanol mixtures as the mobile phase; reverse phase chromatography using trifluoroacetic acid/acetonitrile mixtures as the mobile phase; and ion exchange chromatography using water or an appropriate buffer as the mobile phase. When anion exchange chromatography is performed, preferably a 0-500 mM sodium chloride gradient is employed.

Following oral administration of the pharmaceutical compositions of the present invention, the delivery agent passes though the mucosal barriers of the GI tract and is absorbed into the blood stream where it can be detected in the plasma of subjects. The level of delivery agent in the bloodstream as measured in the plasma is dose-dependent. The delivery agent facilitates the absorption of the drug (active agent) administered therewith (either in the same dosage form, or simultaneously therewith), or sequentially (in either order, as long as both the delivery agent and the drug are administered within a time period which provides both in the same location, e.g., the stomach, at the same time).

In certain preferred embodiments of the invention, a peak plasma concentration ($C_{max}$) of the delivery agent achieved after oral administration is preferably from about 10 to about 250,000 ng/ml, after oral administration, preferably from about 100 to about 125,000, and preferably the peak plasma concentration of the delivery agent is from about 1,000 to about 50,000 ng/ml, after oral administration. More preferably, the peak plasma concentration of the delivery agents of the present invention is from about 5,000 to about 15,000 ng/ml, after oral administration.

The time it takes for the delivery agent to reach a peak in the bloodstream ($t_{max}$) may depend on many factors such as the following: the nature of the unit dose, i.e., solid, liquid, tablet, capsule, suspension; the concentration of delivery agent in the GI tract; the feeding state of the subject; the diet of the subject; the health of the subject and the ratio of delivery agent to the active agent. The delivery agents of the present invention are rapidly absorbed from the gastrointestinal tract when orally administered in an immediate release dosage form, and preferably provide a peak plasma concentration within about 0.1 to about 8 hours after oral administration, and preferably at about 0.1 to about 3 hours after oral administration.

In preferred embodiments, the $t_{max}$ of the delivery agent occurs at about 0.3 to about 1.5 hours after oral administration. In certain embodiments, the delivery agent achieves a $t_{max}$ within about 2 hours after oral administration, and most preferably, within about 1 hour after oral administration.

The amount of delivery agent in the present composition is a delivery effective amount and can be determined by methods known to those skilled in the art. The amount of delivery agent necessary to adequately deliver an active agent into the blood stream of a subject needing the therapeutic effect of that active agent may vary depending on one or more of the following; the chemical nature of the active agent; the chemical structure of the particular delivery agent; the nature and extent of interaction from about the active agent and delivery agent; the nature of the unit dose, i.e., solid, liquid, tablet, capsule, suspension; the concentration of delivery agent in the GI tract; the feeding state of the subject; the diet of the subject; the health of the subject and the ratio of delivery agent to the active agent. In a certain preferred embodiment of the invention, the amount of the delivery agent preferred for the pharmaceutical composition is from about 1 mg to about 2,000 mg delivery agent, more preferably from about 1 mg to about 800 mg of said delivery agent, more preferably from about 50 mg to about 700 mg of said delivery agent, even more preferably from about 70 mg to about 700 mg of said delivery agent, still more preferably from about 100 to about 600 mg.

Preferably, the delivery agent is 4-CNAB. Since the amount of delivery agent required to deliver a particular active agent is variable and the amount of active agent required to produce a desired therapeutic effect is also a variable, the ratio of active agent to delivery agent may vary for different active agent/delivery agent combinations. In certain preferred embodiments of the invention where the oral pharmaceutical composition includes insulin as the active agent and the delivery agent is the compound 4-CNAB, the amount of the delivery agent included in the pharmaceutical composition may be from about 100 mg to about 600 mg of said delivery agent.

In certain preferred embodiments of the invention, the pharmaceutical composition includes insulin as the active agent and the delivery agent is the monosodium salt of 4-CNAB, the ratio of insulin [Units] to delivery agent [mg] ranges from 10:1 [Units/mg] to 1:10 [Units/mg], preferably, the ratio of insulin [Units] to delivery agent [mg] ranges from 5:1 [Units/mg] to 0.5:1 [Units/mg].

Preferred insulin doses in a single administration are about 5 to about 1000 insulin units USP, preferably from about 50 to about 400, more preferably from about 150 to about 400, and still more preferably from about 150 to about 300 units.

The optimum ratio of insulin to delivery agent can vary depending on the delivery agent. Optimizing the ratio of insulin to delivery agent is within the knowledge of one skilled in the art.

In a preferred embodiment of the invention, wherein the pharmaceutical composition includes the compound 4-CNAB as the delivery agent and insulin as the active agent, the composition provides a peak plasma delivery agent concentration within about 0.1 to about 3 hours after oral administration. In certain preferred embodiments where the pharmaceutical composition includes the compound 4-CNAB as the delivery agent and insulin as the active agent, the peak plasma concentration of delivery agent attained is from about 8,000 to about 37,000 ng/ml.

The mechanism by which 4-CNAB facilitates the gastrointestinal absorption of insulin has not yet been fully elucidated. The current working hypothesis is that 4-CNAB interacts with insulin non-covalently, creating more favorable physicochemical properties for absorption. This working hypothesis is provided for explanation purposes only and is not intended to limit the present invention or the appended claims in any way.

In previous patent applications, such as those enumerated above that have been incorporated herein by reference, Emisphere Technologies, Inc. disclosed structures of various delivery agents, comparisons of their effectiveness of absorption and effectiveness of delivery, the preparation of the preferred delivery agent 4-CNAB, its preparation for human studies, and data regarding previous non-clinical and clinical studies involving the delivery agent 4-CNAB.

The delivery agent may be used directly by mixing with the unmodified insulin prior to administration, either in dry powder form or wet granulated together. To this mixture, other pharmaceutically acceptable excipients may be added. The mixture may be then tableted or placed into gelatin capsules containing a unit dose of the active agent and the delivery agent. Alternatively, the delivery agent/insulin mixture may be prepared as an oral solution or suspension. The delivery agent and insulin do not need to be mixed together prior to administration, such that, in certain embodiments, the unit dose of insulin (with or without other pharmaceutically acceptable excipients) is orally administered without the delivery agents of this invention, and the delivery agent is separately orally administered (with or without other pharmaceutically acceptable excipients) before, after, or simultaneously with the insulin.

In certain preferred embodiments, the oral dosage forms of the present invention are solid. The unmodified insulin in dry powder form is stable, and in certain preferred embodiments is simply mixed in a desirable ratio with the delivery agent. The dry powder mixture may then be filled into gelatin capsules, with or without optional pharmaceutical excipients. Alternatively, the unmodified insulin in dry powder form may be mixed with the delivery agent together with optional pharmaceutical excipients, and the mixture may be tableted in accordance with standard tableting procedures known to those having ordinary skill in the art.

The dosage forms of the present invention may be produced by first dissolving insulin and the delivery agent into one solution or separate solutions. The solvent will preferably be an aqueous solution, but organic solvents or aqueous organic solvent mixtures may be used when necessary to solubilize the delivery agent. If two solutions are used, the proportions of each necessary to provide the correct amount of either insulin or delivery agent are combined and the resulting solution may be dried, by lyophilization or equivalent means. In one embodiment of the invention, the oral dosage form may be dried and rehydrated prior to oral administration.

The administration mixtures may be prepared, e.g., by mixing an aqueous solution of the delivery agent with an aqueous solution of insulin just prior to administration. Alternatively, the delivery agent and insulin can be admixed during the manufacturing process. The solutions may optionally contain additives such as phosphate buffer salts, citric acid, acetic acid, gelatin, and gum acacia.

Stabilizing additives may be incorporated into the delivery agent solution. With some drugs, the presence of such additives promotes the stability and dispersibility of the agent in solution. The stabilizing additives may be employed at a concentration ranging from about 0.1 and 5% (W/V), preferably about 0.5% (W/V). Suitable, but non-limiting, examples of stabilizing additives include gum acacia, gelatin, methyl cellulose, polyethylene glycol, carboxylic acids and salts thereof, and polylysine. The preferred stabilizing additives are gum acacia, gelatin and methyl cellulose.

The amount of delivery agent in the present composition is a delivery effective amount and can be determined for any particular delivery agent/active agent combination by methods known to those skilled in the art.

The oral dosage forms of the present invention, containing a mixture of insulin and the delivery agent, e.g., 4-CNAB, or separately containing insulin and the delivery agent, may include additional materials known to those skilled in the art as pharmaceutical excipients. Any excipient or ingredient, including pharmaceutical ingredients or excipients. Such pharmaceutical excipients include, for example, the following: Acidifying agents (acetic acid, glacial acetic acid, citric acid, fumaric acid, hydrochloric acid, diluted hydrochloric acid, malic acid, nitric acid, phosphoric acid, diluted phosphoric acid, sulfuric acid, tartaric acid); Aerosol propellants (butane, dichlorodifluoromethane, dichlorotetrafluoroethane, isobutane, propane, trichloromonofluoromethane); Air displacements (carbon dioxide, nitrogen); Alcohol denaturants (denatonium benzoate, methyl isobutyl ketone, sucrose octacetate); Alkalizing agents (strong ammonia solution, ammonium carbonate, diethanolamine, diisopropanolamine, potassium hydroxide, sodium bicarbonate, sodium borate, sodium carbonate, sodium hydroxide, trolamine); Anticaking agents (see glidant); Antifoaming agents (dimethicone, simethicone); Antimicrobial preservatives (benzalkonium chloride, benzalkonium chloride solution, benzelthonium chloride, benzoic acid, benzyl alcohol, butylparaben, cetylpyridinium chloride, chlorobutanol, chlorocresol, cresol, dehydroacetic acid, ethylparaben, methylparaben, methylparaben sodium, phenol, phenylethyl alcohol, phenylmercuric acetate, phenylmercuric nitrate, potassium benzoate, potassium sorbate, propylparaben, propylparaben sodium, sodium benzoate, sodium dehydroacetate, sodium propionate, sorbic acid, thimerosal, thymol); Antioxidants (ascorbic acid, acorbyl palmitate, butylated hydroxyanisole, butylated hydroxytoluene, hypophosphorous acid, monothioglycerol, propyl gallate, sodium formaldehyde sulfoxylate, sodium metabisulfite, sodium thiosulfate, sulfur dioxide, tocopherol, tocopherols excipient); Buffering agents (acetic acid, ammonium carbonate, ammonium phosphate, boric acid, citric acid, lactic acid, phosphoric acid, potassium citrate, potassium metaphosphate, potassium phosphate monobasic, sodium acetate, sodium citrate, sodium lactate solution, dibasic sodium phosphate, monobasic sodium phosphate); Capsule lubricants (see tablet and capsule lubricant); Chelating agents (edetate disodium, ethylenediamine-tetraacetic acid and salts, edetic acid); Coating agents (sodium carboxymethylcellulose, cellulose acetate, cellulose acetate phthalate, ethylcellulose, gelatin, pharmaceutical glaze, hydroxypropyl cellulose, hydroxypropyl methylcellulose, hydroxypropyl methylcellulose phthalate, methacrylic acid copolymer, methylcellulose, polyethylene glycol, polyvinyl acetate phthalate, shellac, sucrose, titanium dioxide, carnauba wax, microcrystalline wax, zein); Colorants (caramel, red, yellow, black or blends, ferric oxide); Complexing agents (ethylenediaminetetraacetic acid and salts (EDTA), edetic acid, gentisic acid ethanolmaide, oxyquinoline sulfate); Desiccants (calcium chloride, calcium sulfate, silicon dioxide); Emulsifying and/or solubilizing agents (acacia, cholesterol, diethanolamine (adjunct), glyceryl monostearate, lanolin alcohols, lecithin, mono- and di-glycerides, monoethanolamine (adjunct), oleic acid (adjunct), oleyl alcohol (stabilizer), poloxamer, polyoxyethylene 50 stearate, polyoxyl 35 caster oil, polyoxyl 40 hydrogenated castor oil, polyoxyl 10 oleyl ether, polyoxyl 20 cetostearyl ether, polyoxyl 40 stearate, polysorbate 20, polysorbate 40, polysorbate 60, polysorbate 80, propylene glycol diacetate, propylene glycol monostearate, sodium lauryl sulfate, sodium stearate, sorbitan monolaurate, soritan monooleate, sorbitan monopalmitate, sorbitan monostearate, stearic acid, trolamine, emulsifying wax); Filtering aids (powdered cellulose, purified siliceous earth); Flavors and perfumes (anethole, benzaldehyde, ethyl vanillin, menthol, methyl salicylate, monosodium glutamate, orange flower oil, peppermint, peppermint oil, peppermint spirit, rose oil, stronger rose water, thymol, tolu balsam tincture, vanilla, vanilla tincture, vanillin); Glidants and/or anticaking agents (calcium silicate, magnesium silicate, colloidal silicon dioxide, talc); Humectants (glycerin, hexylene glycol, propylene glycol, sorbitol); Plasticizers (castor oil, diacetylated monoglycerides, diethyl phthalate, glycerin, mono- and di-acetylated monoglycerides, polyethylene glycol, propylene glycol, triacetin, triethyl citrate); Polymers (e.g., cellulose acetate, alkyl celloloses, hydroxyalkylcelloloses, acrylic polymers and copolymers); Solvents (acetone, alcohol, diluted alcohol, amylene hydrate, benzyl benzoate, butyl alcohol, carbon tetrachloride, chloroform, corn oil, cottonseed oil, ethyl acetate, glycerin, hexylene glycol, isopropyl alcohol, methyl alcohol, methylene chloride, methyl isobutyl ketone, mineral oil, peanut oil, polyethylene glycol, propylene carbonate, propylene glycol, sesame oil, water for injection, sterile water for injection, sterile water for irrigation, purified water); Sorbents (powdered cellulose, charcoal, purified siliceous earth); Carbon dioxide sorbents (barium hydroxide lime, soda lime); Stiffening agents (hydrogenated castor oil, cetostearyl alcohol, cetyl alcohol, cetyl esters wax, hard fat, paraffin, polyethylene excipient, stearyl alcohol, emulsifying wax, white wax, yellow wax); Suspending and/or viscosity-increasing agents (acacia, agar, alginic acid, aluminum monostearate, bentonite, purified bentonite, magma bentonite, carbomer 934p, carboxymethylcellulose calcium, carboxymethylcellulose sodium, carboxymethycellulose sodium 12, carrageenan, microcrystalline and carboxymethylcellulose sodium cellulose, dextrin, gelatin, guar gum, hydroxyethyl cellulose, hydroxypropyl cellulose, hydroxypropyl methylcellulose, magnesium aluminum silicate, methylcellulose, pectin, polyethylene oxide, polyvinyl alcohol, povidone, propylene glycol alginate, silicon dioxide, colloidal silicon dioxide, sodium alginate, tragacanth, xanthan gum); Sweetening agents (aspartame, dextrates, dextrose, excipient dextrose, fructose, mannitol, saccharin, calcium saccharin, sodium saccharin, sorbitol, solution sorbitol, sucrose, compressible sugar, confectioner's sugar, syrup); Tablet binders (acacia, alginic acid, sodium carboxymethylcellulose, microcrystalline cellulose, dextrin, ethylcellulose, gelatin, liquid glucose, guar gum, hydroxypropyl methylcellulose, methycellulose, polyethylene oxide, povidone, pregelatinized starch, syrup); Tablet and/or capsule diluents (calcium carbonate, dibasic calcium phosphate, tribasic calcium phosphate, calcium sulfate, microcrystalline cellulose, powdered cellulose, dextrates, dextrin, dextrose excipient, fructose, kaolin, lactose, mannitol, sorbitol, starch, pregelatinized starch, sucrose, compressible sugar, confectioner's sugar); Table disintegrants (alginic acid, microcrystalline cellulose, croscarmellose sodium, corspovidone, polacrilin potassium, sodium starch glycolate, starch, pregelatinized starch); Tablet and/or capsule lubricants (calcium stearate, glyceryl behenate, magnesium stearate, light mineral oil, polyethylene glycol, sodium stearyl fumarate, stearic acid, purified stearic acid, talc, hydrogenated vegetable oil, zinc stearate); Tonicity agent (dextrose, glycerin, mannitol, potassium chloride, sodium chloride); Vehicle: flavored and/or sweetened (aromatic elixir, compound benzaldehyde elixir, iso-alcoholic elixir, peppermint water, sorbitol solution, syrup, tolu balsam syrup); Vehicle: oleaginous (almond oil, corn oil, cottonseed oil, ethyl oleate, isopropyl myristate, isopropyl palmitate, mineral oil, light mineral oil, myristyl alcohol, octyldodecanol, olive oil, peanut oil, persic oil, seame oil, soybean oil, squalane); Vehicle: solid carrier (sugar spheres); Vehicle: sterile (bacteriostatic water for injection, bacteriostatic sodium chloride injection); Viscosity-increasing (see suspending agent); Water repelling agent (cyclomethicone, dimethicone, simethicone); and Wetting and/or solubilizing agent (benzalkonium chloride, benzethonium chloride, cetylpyridinium chloride, docusate sodium, nonoxynol 9, nonoxynol 10, octoxynol 9, poloxamer, polyoxyl 35 castor oil, polyoxyl 40, hydrogenated castor oil, polyoxyl 50 stearate, polyoxyl 10 oleyl ether, polyoxyl 20, cetostearyl ether, polyoxyl 40 stearate, polysorbate 20, polysorbate 40, polysorbate 60, polysorbate 80, sodium lauryl sulfate, sorbitan monolaureate, sorbitan monooleate, sorbitan monopalmitate, sorbitan monostearate, tyloxapol). This list is not meant to be exclusive, but instead merely representative of the classes of excipients and the particular excipients which may be used in oral dosage forms of the present invention.

Following administration, the insulin present in the dosage unit form is absorbed into the circulation. The bioavailability of the insulin is readily assessed by measuring a known pharmacological activity in blood, e.g., decreased blood glucose. Further physiologic effects of the insulin can be measured using tests, for example, measurement of plasma C-peptide concentration. Alternately, the circulating levels of the insulin itself can be measured directly. Similarly, levels of 4-CNAB or other delivery agent in the blood can be measured.

In order that this invention may be better understood, the following examples are set forth. These examples are for the purpose of illustration only and are not to be construed as limiting the scope of the invention in any manner.

Detailed Description of Preferred Embodiments

In order that this invention may be better understood, the following examples are set forth. These examples are for the purpose of illustration only and are not to be construed as limiting the scope of the invention in any manner.

EXAMPLE 1

Preparation of the Delivery Agent 4-CNAB

The compound corresponding to the following structure may be prepared as described below:

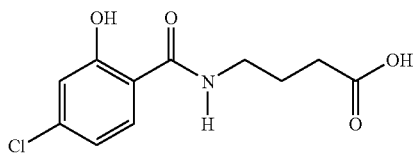

4-Chlorosalicylic acid (10.0 g, 0.0579 mol) was added to a one-neck 250 ml round-bottomed flask containing about 50 ml methylene chloride. Stirring was begun and continued for the remainder of the reaction. The coupling agent 1,1-carbonyldiimidazole (9.39 g, 0.0579 mol) was added as a solid in portions to the flask. The reaction was stirred at room temperature for approximately 20 minutes after all of the coupling agent had been added and then ethyl-4-aminobutyrate hydrochloride (9.7 g, 0.0579 mol) was added to the flask with stirring. Next, triethylamine (10.49 ml, 0.0752 mol) was added dropwise from an addition funnel. The addition funnel was rinsed with methylene chloride. The reaction was allowed to stir at room temperature overnight.

The reaction was poured into a separatory funnel and washed with 2N HCl and an emulsion formed. The emulsion was left standing for two days and was then filtered through celite in a fritted glass funnel. The filtrate was put back in a separatory funnel to separate the layers. The organic layer was dried over sodium sulfate, which was then filtered off and the filtrate concentrated by rotary evaporation. The resulting solid material was hydrolyzed with 2N NaOH, stored overnight under refrigeration, and then hydrolyzing resumed. The solution was acidified with 2N HCl and the solids that formed were isolated, dried under vacuum, and recrystallized twice using methanol/water. Solids precipitated out overnight and were isolated and dried. The solids were dissolved in 2N NaOH and the pH of the sample was brought to pH 5 with 2N HCl. The solids were collected and HPLC revealed a single peak. These solids were then recrystallized in methanol/water, isolated, and then dried under vacuum, yielding 4.96 g (33.0%) of 4-(4 chloro-2-hydroxybenzoyl)aminobutyric acid, ($C_{11}H_{12}ClNO_4$; Molecular weight 257.67). A melting point of 131-133° C. was determined. Combustion analysis revealed the following content: % C: 51.27 (calc.), 51.27 (found); % H, 4.69 (calc.), 4.55 (found); % N, 5.44 (calc.), 5.30 (found). Proton H NMR Analysis revealed: ($d_6$-DMSO): d 13.0, s, 1H (COOH); d 12.1, s, 1H (OH); d 8.9, t, 1H (NH); d 7.86, d, 1H (H ortho to amide); d 6.98, d, 1H (H ortho to phenol OH); d 6.96, d, 1H, (H meta to amide); d 3.33, m, 2H ($CH_2$ adjacent to NH); d 2.28, t, 2H ($CH_2$ adjacent to COOH); d 1.80, m, 2H (aliphatic $CH_2$ beta to NH and $CH_2$ beta to COOH).

4-CNAB Preparation for Human Studies

4-CNAB for the human dosings (Monosodium N-(4-chlorosalicyloyl)-4-amino-butyrate) was made under good manufacturing practices (GMP) conditions by Regis Technologies, Inc. (Morton Grove, Ill.) according to the methods of International Publication No. WO 00/46182 except that the starting material 4-chlorosalicylic acid (purchased from Ihara Chemical Industry Co. Inc, Ltd., Tokyo, Japan and Aapin Chemicals Ltd., Oxfordshire, UK) was used and converted to the amide via a methyl ester using 0.14 equivalents sulfuric acid in methanol and then about 4 equivalents ammonia in methanol. The allylating agent used was ethyl-4-bromobutyrate.

The monosodium salt of 4-CNAB was made according to the following method on a 40 kilogram scale. 4-CNAB free acid (500 g, 1.94 mol, FW=257.67) was charged to a 22 L five neck round bottom flask. The flask was equipped with an overhead stirrer, a thermocouple temperature read out, a reflux condenser and a heating mantle, and was placed under nitrogen. Reagent grade acetone (13 L) was added to the reactor and the mixture was agitated. The 4-CNAB/acetone mixture was heated to 50° C. to dissolve any solids. A hazy brown solution was achieved.

The 50° C. solution was pumped through a warm pressure filter (dressed with Whatman #1 filter paper, ~5 microns, 18.5 sq. in. area) into a clean 22 L reactor to remove sodium chloride and other insolubles. The pressure dropped across the filter to about 20 psig at the end of filtration. The reactor containing the clear yellow filtrate was agitated and heated. At 50° C. the reactor was removed from heat.

The clear filtrate was charged with 50% sodium hydroxide solution (155 g, 1.94 mol) as rapidly as possible, while maintaining a vigorous agitation. (An overcharge will result in the undesirable formation insoluble disodium salts. A slight undercharge is preferable because the free acid is removed during the final filtration step.) The reaction mixture exothermed to approximately 52° C. Precipitates formed and the product gelled before becoming clear again. After the base addition was completed and the temperature leveled, the solution became cloudy and increased in viscosity. The reaction was refluxed for 2 hours at 60° C., while agitating vigorously. The reaction mixture continued to thicken, forming solid chunks. The slurry became light pink and foamed. The reactor contents were cooled to ambient temperature over 3 to 4 hours. The ambient temperature was held for 30 minutes. The precipitated solids were isolated on a filter funnel. The isolated product was not washed. The resulting 4-CNAB monosodium salt was dried in vacuo at 40 to 50° C. for 16 to 24 hours to give 490 grams (1.75 mol, 90% yield, FW=279.65).

The insulin for the subcutaneous injection was HUMULIN® R injection insulin from Eli Lilly and Company (Indianapolis, Ind.).

All capsules containing 200 mg 4-CNAB and 150 insulin units USP were prepared as follows. First, the total amount of delivery agent material necessary for filling the delivery agent alone capsules and the delivery agent plus insulin composition capsules was prepared by weighing 3160 g of 4-CNAB. The 3160 g 4-CNAB was then milled in a Quadro comil, model 197S mill with screen number 2A 050 G 037 19 136 (1270 micron). Next, 1029 g of the milled 4-CNAB was passed through a #35 mesh screen. Then, the pass through screened material was transferred into a 4 quart shell and blended using for example, a V blender, at 25 rpm for 10.2 minutes. The resultant blended material was used to fill capsules. In this case, a Fast Cap Capsule Filler was used with a size 3 Fast Cap Encapsulation tray. The empty capsules weighed approximately 48 mg each and were filled with an average fill weight of 205.6 mg of 4-CNAB alone. Thus, the dose of the delivery agent alone capsules was 205.6 mg.

The insulin compositions were prepared by first dispensing 31.8 g of recombinant human zinc crystalline insulin (Potency 26.18 Units per mg) (proinsulin derived (recombinant DNA origin) USP quality) from Eli Lilly and Company (Indianapolis, Ind.) into an appropriately sized plastic bag. Next, sequential 30 g additions of the milled and screened 4-CNAB were added to the bag until approximately 510 g had been added. The bag was thoroughly mixed after each 30 g addition of 4-CNAB by shaking and inversion. In order to add and mix the next 532.5 g of 4-CNAB, the 541.8 g mixture of insulin and 4-CNAB was transferred to a V blender and mixed again at 25 rpm for 10.2 minutes. Next, the remaining 4-CNAB was added to the blender and the entire mixture was mixed in the blender at 25 rpm for 10.2 minutes. Finally, the resulting composition was dispensed as described above into empty capsules. The final capsules contained an average of 5.7 mg insulin (equivalent to 150 units insulin) and 200.5 mg of 4-CNAB or a ratio of 1:57.3, insulin: 4-CNAB. Multiple samples of the final blend were run on HPLC to verify uniformity and were found to be uniform.

EXAMPLE 2

Previous Non-clinical Studies with 4-CNAB and Insulin/4-CNAB

The present invention comprising compositions of insulin and the delivery agent 4-CNAB was evaluated for safety and toxicity in a non-clinical program that included pharmacological screening, pharmacokinetic profiling, and toxicity assessments in rats and monkeys. In general, animal physiological responses to 4-CNAB alone and to Insulin/4-CNAB were comparable. Pharmacokinetic studies in mice, rats and monkeys have shown that 4-CNAB is absorbed rapidly following oral administration, and subsequently cleared from the body. 4-CNAB did not demonstrate potential activity in any of the primary molecular targets evaluated in receptor binding screening assays. Four genotoxicity studies have been conducted with 4-CNAB, with no positive findings. Based on 14-day oral repeated dose toxicity studies, the NOAEL (No-Adverse Effect Level) was estimated to be 500 mg/kg in Sprague-Dawley rats, and 400 mg/kg in rhesus monkeys.

In toxicology studies, 4-CNAB doses from 400 mg to 2000 mg were evaluated. Following 14-day oral repeated dose toxicity studies in rats and monkeys, the estimated No Adverse Effect Level (NOAEL) for 4-CNAB was 500 mg/kg in Sprague-Dawley rats and 400 mg/kg in rhesus monkeys; therefore, the monkey appeared to be the most sensitive species. The highest proposed dose of 2000 mg 4-CNAB in man (<30 mg/kg) is 12-16 fold lower than the NOAEL in monkeys (i.e., NOAEL=400 mg/kg 4-CNAB alone and in combination with 15 U/kg insulin). The absolute bioavailability of insulin in monkeys was about 1% or less. In the toxicology studies, there were no findings in rats attributed to insulin at an oral dose level of 15 U/kg in combination with 4-CNAB doses as high as 2000 mg/kg. In monkeys, an insulin dose of 15 U/kg was associated with a single hypoglycemic episode in combination with a 4-CNAB dose of 1200 mg/kg in one monkey; there were no effects at 15 U/kg insulin in combination with lower doses.

Non-clinical studies in rats and monkeys demonstrated that, over the range tested, insulin absorption increases with increasing doses of 4-CNAB. Similarly, for a fixed oral dose of 4-CNAB, insulin absorption increases with increasing doses of insulin. Oral insulin absorption was evaluated in rats at varying doses of both insulin and 4-CNAB. Significant increases in serum insulin concentrations were observed following the administration of insulin at doses of 4.55, 6.5, 9.75 and 13 Units/kg in the presence of a fixed 4-CNAB dose (200 mg/kg). The mean peak serum insulin levels were 31, 44, 85 and 132 µU/mL, respectively. Insulin absorption was dose dependent and increased as the dose of insulin increased. Oral administration of aqueous solutions of insulin alone (13 Units/kg) or 4-CNAB alone (200 mg/kg) did not result in any significant increases in serum insulin levels. Significant increases in serum insulin concentrations were also observed following the administration of 4-CNAB at doses of 50, 100, 200, and 300 mg/kg in the presence of a fixed insulin dose (13 Units/kg). The mean peak serum insulin levels were 9, 39, 103 and 157 µU/mL, respectively. Insulin absorption was dose dependent and increased as the dose of 4-CNAB increased.

Based on the above non-clinical information, the starting insulin dose of 150 insulin Units USP (which is about 7-fold lower than the 15 U/kg no effect dose in monkey) was selected.

EXAMPLE 3

This example describes the procedure for preparing Insulin/4-CNAB capsules. The 4-CNAB as prepared above was first screened through a 35 mesh screen. The required amount of the screened 4-CNAB was weighed and was kept in a covered weighing boat. The required amount of insulin was weighed and was kept in a covered weighing boat.

The insulin from above was screened through the 35 mesh screen onto the same mortar, and approximately 2.0 grams of the 4-CNAB from above was screened on top of the insulin using the same 35 mesh screen. The contents of the mortar was mixed by light trituration for about 3 minutes with a glass mortar, with a spatula used for scraping, as necessary. The 4-CNAB from above was continued to be screened through the same 35 mesh screen in small portions equivalent to the volume of material in the mortar. After each addition, the contents of the mortar were mixed for about 3 minutes.

After the final addition, the contents of the mortar was mixed by light trituration with a glass mortar for about 2 minutes, with a spatula used for scraping, as necessary. The final blend was transferred into a weighing boat for capsule filling and hand-filled into the capsules.

EXAMPLE 4

In this example, the oral insulin capsule(s) described herein were orally administered to twenty human subjects with diabetes at night before going to sleep.

The rationale for nighttime administration is as follows. The clinical studies reported herein with oral insulin in type 2 diabetic patients demonstrated a hypoglycemic effect of short duration. This probably indicates that the half-life of systemic circulating insulin provided by oral insulin is short in order to affect peripheral glucose disposal. It was hypothesized that orally administered insulin may, however, have a more profound effect on hepatic glucose production, which is responsible for the fasting blood glucose levels, due to portal delivery of the oral insulin. This study was thus to determine whether the metabolic effect of orally administered insulin is more prolonged than the actual half-life of insulin in plasma.

In type 2 diabetics, blood glucose levels are often elevated after an overnight fast, presumably because of unrestrained glucose production by the liver as a result of a combination of insulin resistance and insufficient insulin secretion, which is the hallmark of the disease. Elevated blood glucose levels can lead to a vicious cycle to perpetuate the severity of a diabetic's condition because, if blood glucose is elevated for an extended period of time, a corresponding "wear and tear" on the cells in the pancreas that secrete insulin to regulate blood glucose levels is possible. Thus, if a treatment were to spare insulin producing cell function, this "rest" to the cells may provide for long-term protection against development of overt diabetes or progression from non-insulin dependent diabetes to insulin dependent diabetes. It was, therefore, proposed to study the effect of bedtime oral insulin on hepatic glucose production and hence fasting blood glucose.

In accordance with the above, this example reports the results of an open-label, single-dose, crossover study comparing the safety of orally administered Insulin/4-CNAB formulation in two groups of subjects with type 2 diabetes mellitus—one in the fasting state and one with a standard meal. The objectives were (1) to compare the safety, pharmacokinetics and pharmacodynamics of orally administered Insulin/4-CNAB in fasting type 2 diabetic subjects, and (2) to compare blood glucose, insulin and C-peptide levels after a standard meal with diet or regular medication with blood glucose, insulin and C-peptide levels after a standard meal with Insulin/4-CNAB.

The focus of this example is the assessment of the safety, pharmacokinetics and pharmacodynamics of insulin/4-CNAB, administered orally at bedtime, to type 2 diabetic subjects. The purpose of the study was to determine if the administration of oral insulin at bedtime could exert effects on overnight-fasting glucose homeostasis and insulin secretion. The postulated mode of action (e.g., suppressing the liver production of glucose, and thus preventing beta cell damage or even death, leading to exacerbation of dysfunction of insulin production) was the basis for the design of the study.

In the first part of the study, twenty-four human diabetic subjects (patients) of age 35-70 years, with elevated fasting blood glucose levels but in otherwise good general health on the basis of a medical history, physical examination and clinical laboratory studies, participated in the study and were studied in the overnight-fasted state on two occasions, separated by an interval of at least 7 days. Subjects who were on anti-diabetic drugs, e.g., Acarbose or Metformin, did not take their medication 24 hours prior to the start of the trial. The following treatment conditions were studied:

Group 1: twelve (12) type 2 diabetic subjects: (a) oral insulin/4-CNAB—fasted subjects, and (b) empty capsule—fasted subjects.

Group 2: twelve (12) type 2 diabetic subjects: (a) standard meal with regular medication, and (b) oral human insulin/4-CNAB prior to standard meal.

In the second part of the study, relating to the safety of insulin/4-CNAB administered orally at bedtime, only twenty of the twenty-four subjects participated, an additional four subjects not being included due to logistical considerations. These twenty subjects took oral insulin capsules at night before going to sleep. The trial took place at the home of the subject, and the rationale to conduct the trial at the patient's own environment was based on the facts that glucose homeostasis is best reflected when conducted in a familiar environment and that glucose homeostasis changes significantly with hospitalization.

Fasting blood glucose, insulin and C-peptide levels were measured at 7:00 a.m. for three days to establish baseline levels. On two successive nights and mornings before taking the capsule, the subjects measured their glucose levels with a glucometer (supplied). If the subject's fasting glucose levels were >120 mg/dl on the first two mornings, the subject took the insulin capsule(s) on the third night. If, on the first two successive mornings, the patient's fasting blood glucose was not greater than 120 mg/dl, then the patient was dismissed from the study and all final study procedures were performed as per the protocol.

The subjects ate their regular dinner at home, as every evening, between the hours of 7:00 and 8:00 P.M. If the subjects usually took medication for the diabetes (e.g., Metformin or Acarbose) in the evening, they took their usual doses. At 11:00 p.m. (at least two hours after dinner), the subjects took one oral insulin dose that contained the following ingredients: 300 mg 4-CNAB and insulin according to the dose (200-400 U) that the subject received during the first phase of the trial. If the subject had received 200 U insulin in the first phase of the trial and there was no drop in blood glucose level (<15% reduction), that subject now received 300 U of insulin. If the subject had received 300 U insulin in the first phase of the trail and there was no drop in blood glucose level (<15% reduction), that subject now received 400 U of insulin. None of the subjects received more than 400 U of insulin. The capsules were prepared by AAI and have shown stability.

The subjects' blood glucose levels were checked with a glucometer before the subjects took the medication. In addition, blood was taken for further blood glucose levels, insulin and C-peptide. Orange juice was readily available for treatment in the unlikely event of hypoglycemia. During sleep, the subjects wore a Glucowatch (which monitors blood glucose and measures and records blood glucose levels at regular intervals), which is equipped with an alarm that is triggered when blood glucose levels reach predetermined blood glucose levels (hypoglycemic levels) determined by the investigator or patient. In the morning (e.g., at 7:00 a.m.), the subjects' blood glucose levels were checked with the glucometer, and additional blood samples were taken for further blood glucose levels, insulin and C-peptide.

The blood samples from the night before were stored in the refrigerator at home, and in the morning the nurse brought the samples of blood (from the night and the morning) to the lab for analysis.

Figure 4:
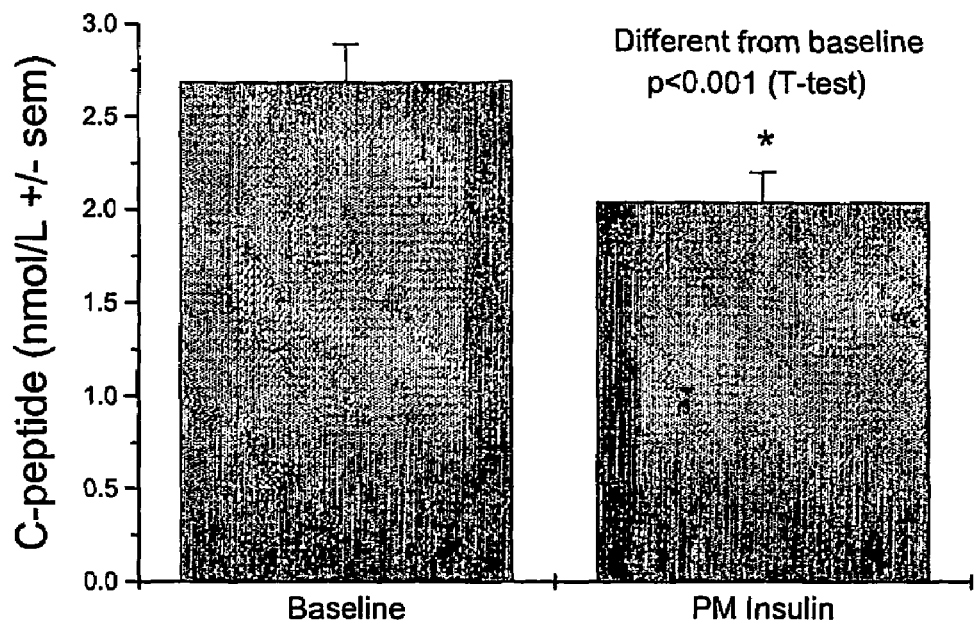
FIG. 4 is a bar graph showing the effect of nighttime dosing of insulin and 4-CNAB on blood C-peptide concentration.
Figure 5:
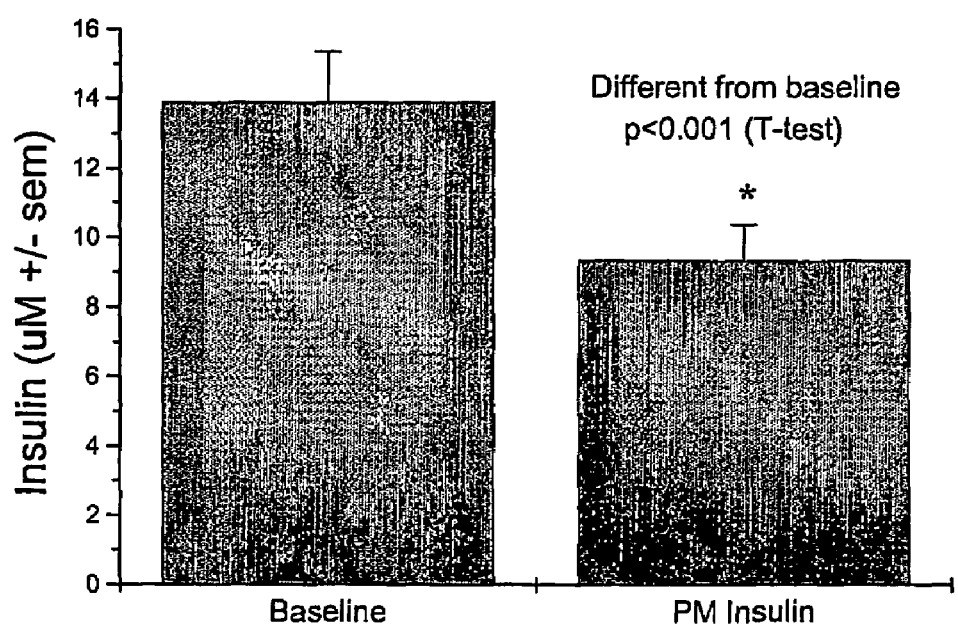
FIG. 5 is a bar graph showing the effect of nighttime dosing of insulin and 4-CNAB on blood insulin concentration.

The results of the nighttime oral insulin study reported as the example herein (fasting blood glucose, insulin and C-peptide measured at approximately 7:00 a.m. and compared to the patient's own baseline levels) are set forth in FIGS. 1-5. The results are reported by patient with numeric values in FIGS. 1 and 2 ($\mu$U/ml), and are graphically represented in FIGS. 3-5. FIG. 1 shows data for blood glucose, insulin and C-peptide collected in the morning after nighttime dosing of insulin/4-CNAB for each subject compared to that subject's own baseline levels, and FIG. 2 shows data for insulin and C-peptide collected at night prior to nighttime dosing of insulin and 4-CNAB for each subject. FIGS. 3-5 are bar graphs showing the effect of nighttime dosing of insulin/4-CNAB on blood glucose concentration, blood C-peptide concentration and blood insulin concentration, respectively.

The increase in insulin level appeared 10-30 minutes after ingestion of the capsules and preceded the drop in glucose level. The 4-CNAB showed a rapid absorption, its concentration peaking at about 30 minutes post administration. There were no serious adverse effects in the course of the study, and the 4-CNAB was well tolerated.

The overnight study demonstrated that the metabolic effect of a single dose of oral insulin was still apparent in the morning, i.e., about eight hours after administration. As a result of the evening dose, there was a decrease in blood glucose output from the liver. As shown in FIG. 2 (effect on blood glucose), there was no statistically significant difference between the baseline blood glucose levels and the blood glucose levels in the patients after administration of the nighttime oral insulin capsules. Blood glucose measured the morning after administration decreased by 6% from baseline levels, i.e., from 133.78±40.53 mg/dl to 125.78±42.99 ($p=0.017$). The subjects who received the Insulin/4-CNAB capsule with their standard meal showed the same blood glucose level after a standard meal as with regular medication such as Acarbose or Metformin.

On the other hand, in all patients, a statistically significant reduction in C-peptide and insulin was detected in the morning (while the glucose levels were not statistically significantly altered). A consistent compensatory decline in C-peptide levels from baseline by a mean of 24%, i.e., from 2.69±0.88 ng/ml to 2.04±0.71 ($p<0.001$) indicated that there was less activity in the beta cells that secrete endogenously produced insulin. Plasma insulin levels were reduced by a mean of 33%, i.e., from 13.90±6.44 $\mu$U/ml to 9.35±4.52 ($p<0.001$). These results are graphically depicted in FIGS. 3 and 4, respectively. The absorption of insulin thus caused a statistically significant drop in C-peptide level, indicating decreased endogenous insulin secretion, due to decreased insulin demand resulting from decreased hepatic glucose output.

Thus, administration of bedtime insulin caused a reduction in plasma insulin level the morning after ingestion of the insulin/4-CNAB capsule compared with that measured the two mornings when the subjects came to the clinic for the first stage of the trial. The bedtime dosing of oral insulin resulted in suppressed overnight fasting insulin demand and may improve insulin sensitivity (unchanged fasting glycemia with reduced systemic hyperinsulinemia).

The interpretation of these results is that a "boost" of exogenous insulin at nighttime allows the patients' beta cells to rest and produce less insulin to achieve the same glycemic level. The suggested clinical implication is that if such treatment were to be given (bed time oral insulin) alone, it is likely to spare beta cell function as these cells become dysfunctional (and eventually die from exhaustion and/or glucose toxicity. This significance is supported by several reported studies which have shown that by intervening "aggressively" with insulin at early stages of the disease (such as IGT or "impaired glucose tolerance" stage), by giving insulin even for a short time such as two week duration, that this "rest" to the cells may provide for long term protection to develop overt diabetes.

It was further seen in this study that none of the patients had a clinically significant hypoglycemic episode, despite the fact that the insulin was administered to the patients in the fasting state and with continued fasting. This result supports the conclusion that the administration of oral insulin formulations as described herein will be safer in terms of hypoglycemia than administration of insulin via a non-oral (portal) route.

In the preceding specification, the invention has been described with reference to specific exemplary embodiments and examples thereof. It will, however, be evident that various modifications and changes may be made thereto without departing from the broader spirit and scope of the invention as set forth in the claims that follow. The specification and drawings are accordingly to be regarded in an illustrative manner rather than a restrictive sense.

While we have hereinbefore described a number of embodiments of this invention, it is apparent that our basic constructions can be altered to provide other embodiments which utilize the processes and compositions of this invention. Therefore, it will be appreciated that the scope of this invention is to be defined by the claims appended hereto rather than by the specific embodiments which have been presented hereinbefore by way of example.

What is claimed is:

1. A method of treating a mammal which has impaired glucose tolerance or early stage diabetes mellitus, comprising orally administering to said mammal, at or shortly before bedtime, a therapeutically effective dose of a pharmaceutical formulation comprising insulin and the delivery agent 4-CNAB in an amount which facilitates absorption of said insulin from the gastrointestinal tract of said mammal.

2. The method of claim 1 wherein the treating comprises substantially reducing the incidence of beta cell death or dysfunction.

3. The method of claim 1 wherein the treating comprises long term reduction in the incidence of developing overt diabetes.

4. The method of claim 1 wherein the treating comprises delaying the onset of overt or insulin dependent diabetes.

5. The method of claim 1, wherein the mammal is a rodent, dog, cat, sheep, pig, cow, horse or human.

6. The method of claim 5, wherein the mammal is a human.

7. The method of claim 1, wherein the oral pharmaceutical formulation is administered on a chronic basis.

8. The method of claim 1, wherein the oral pharmaceutical formulation is administered nightly for at least two weeks.

9. The method of claim 5, which provides a lowering of morning or fasting insulin levels of at least about 20%.

10. The method of claim 5, which achieves a therapeutically effective reduction in blood glucose after oral administration to a human diabetic patient, and which provides a ratio of portal vein to peripheral blood insulin concentration from about 2.5:1 to about 6:1.

11. The method of claim 5, wherein the dose of the pharmaceutical composition is administered through a dosage form that is solid.

12. The method of claim 1, wherein the dose of insulin contained in the dosage form is from about 50 Units to about 600 Units.

13. The method of claim 1, wherein the dose of unmodified insulin is from about 100 Units to about 400 Units insulin.

14. The method of claim 1, wherein the dose of unmodified insulin is from about 150 Units to about 300 Units.

15. The method of claim 1, wherein the dosage form(s) begin delivering insulin into the portal circulation (via absorption through the mucosa of the gastrointestinal tract) to achieve peak levels within about 30 minutes or less.

16. A method of treating manimals having impaired glucose tolerance or early stage diabetes mellitus, comprising,
orally administering to said mammal, at or shortly before bedtime, insulin and the delivery agent 4-CNAB in an amount which facilitates absorption of said insulin from the gastrointestinal tract of said mammal such that a statistically significant decrease in C-peptide levels from a mean baseline level is achieved in said mammal when said C-peptide level is measured about 8 hours after said oral administration of insulin.

17. The method of claim 16, wherein said C-peptide levels when measured are decreased by a mean of about 24%.

18. The method of claim 16, wherein plasma insulin levels are reduced by a statistically significant degree from baseline when measured about 8 hours after said oral adnilnistration of insulin.

19. The method of claim 18, wherein said plasma insulin levels are reduced by a mean of about 33% from baseline when measured about 8 hours after said oral administration of insulin.

20. The method of claim 16, wherein blood glucose levels are reduced by a statistically insignificant degree from baseline when measured about 8 hours after said oral administration of insulin.

21. The method of claim 20, wherein said blood glucose levels are reduced by a mean of about 6% from baseline when measured about 8 hours after said oral administration of insulin.

22. The method of claim 16, wherein said oral administration of insulin comprises a dose of from about 200 to about 400 units of insulin.

23. The method of claim 16, wherein the amount of 4-CNAB is about 300 mg.

24. A method of treating mammals having impafred glucose tolerance or early stage diabetes mellitus, comprising orally administering to said mammal, at or shortly before bedtime, an unmodified insulin and the delivery agent 4-CNAB in an amount which facilitates absorption of said insulin from the gastrointestinal tract such that a statistically significant decrease in C-peptide levels from a mean baseline level is achieved in said mammal when said C-peptide level is measured about 8 hours after said oral administration of insulin.

25. The method of claim 1, wherein said oral administration provides an insulin $t_{max}$ at a time point from about 0.1 to about 1.5 hours after said oral administration, such that a statistically significant decrease in C-peptide levels from baseline is achieved in said mammal when said C-peptide level is measured about 8 hours after said oral administration of insulin.

26. The method of claim 1, wherein plasma insulin levels are reduced by a statistically significant degree from baseline when measured about 8 hours after said oral administration of insulin.

27. The method of claim 1 wherein the treating comprises reducing beta cell function.

28. The method of claim 1, wherein the pharmaceutical formulation comprises about 300 mg of 4-CNAB.

29. A method of treating a mammal which has impaired glucose tolerance or early stage diabetes mellitus, comprising orally administering to said mammal, at or shortly before bedtime, a therapeutically effective dose of a pharmaceutical formulation comprising an unmodified insulin and the delivery agent 4-CNAB in an amount which facilitates absorption of said insulin from the gastrointestinal tract of said mammal.

30. The method of claim 1, wherein C-peptide levels of said mammal are decreased by a mean of about 24% when measured about 8 hours after said oral administration of insulin.

31. The method of claim 1, wherein plasma insulin levels of said mammal are reduced by a mean of about 33% when measured about 8 hours after said oral administration of insulin.

32. The method of claim 1, wherein blood glucose levels of said mammal are reduced by a mean of about 6% when measured about 8 hours after said oral administration of insulin.

33. The method of claim 16, wherein said mammal is a human.

34. The method of claim 24, wherein said C-peptide levels when measured are decreased by a mean of about 24%.

35. The method of claim 24, wherein plasma insulin levels are reduced by a statistically significant degree from baseline when measured about 8 hours after said oral administration of insulin.

36. The method of claim 35, wherein said plasma insulin levels are reduced by a mean of about 33% from baseline when measured about 8 hours after said oral administration of insulin.

37. The method of claim 24, wherein blood glucose levels are reduced by a statistically insignificant degree from baseline when measured about 8 hours after sald oral administration of insulin.

38. The method of claim 37, wherein said blood glucose levels are reduced by a mean of about 6% from baseline when measured about 8 hours after said oral administration of insulin.

39. The method of claim 24, wherein said oral administration of insulin comprises a dose of from about 200 to about 400 units of insulin.

40. The method of claim 24, wherein said insulin comprises a dose of from about 100 to about 400 units of insulin.

41. The method of claim 24, wherein the amount of 4-CNAB is about 300 mg.

42. The method of claim 24, wherein the mammal is a human.

43. The method of claim 29, wherein the mammal is a human.

44. The method of claim 29, wherein the oral pharmaceutical formulation is administered on a chronic basis.

45. The method of claim 29, wherein the oral pharmaceutical formulation is administered nightly for at least two weeks.

46. The method of claim 29, which provides a lowering of morning or fasting insulin levels of at least about 20%.

47. The method of claim 29, which achieves a therapeutically effective reduction in blood glucose after oral administration to a human diabetic patient, and which provides a ratio of portal vein to peripheral blood insulin concentration from about 2.5:1 to about 6:1.

48. The method of claim 29, wherein the dose of the pharmaceutical composition is administered through a dosage form that is solid.

49. The method of claim 29, wherein the dose of insulin contained in the dosage form is from about 50 Units to about 600 Units.

50. The method of claim 29, wherein the dose of unmodified insulin is from about 100 Units to about 400 Units insulin.

51. The method of claim 29, wherein the dose of unmodified insulin is from about 150 Units to about 300 Units.

52. The method of claim 29, wherein the dosage form(s) begin delivering insulin into the portal circulation (via absorption through the mucosa of the gastrointestinal tract) to achieve peak levels within about 30 minutes or less.

53. The method of claim 29, wherein said oral administration provides an insulin $t_{max}$ at a time point from about 0.1 to about 1.5 hours after said oral administration, such that a statistically significant decrease in C-peptide levels from baseline is achieved in said mammal when said C-peptide level is measured about 8 hours after said oral administration of insulin.

54. The method of claim 29, wherein plasma insulin levels are reduced by a statistically significant degree from baseline when measured about 8 hours after said oral administration of insulin.

55. The method of claim 29, wherein C-peptide levels of said mammal are decreased by a mean of about 24% when measured about 8 hours after said oral administration of insulin.

56. The method of claim 29, wherein plasma insulin levels of said mammal are reduced by a mean of about 33% when measured about 8 hours after said oral administration of insulin.

57. The method of claim 29, wherein blood glucose levels of said mammal are reduced by a mean of about 6% when measured about 8 hours after said oral administration of insulin.

58. The method of claim 29, wherein said formulation comprises from about 200 to about 400 units of insulin.

59. The method of claim 58, wherein the pharmaceutical formulation comprises about 300 mg of 4-CNAB.

* * * * *